United States Patent [19]

Hung

[11] 4,175,557
[45] Nov. 27, 1979

[54] POLYMERIC SHEETS
[75] Inventor: John H. Hung, Monroe, N.Y.
[73] Assignee: International Paper Company, New York, N.Y.
[21] Appl. No.: 735,671
[22] Filed: Nov. 1, 1976

Related U.S. Application Data

[63] Continuation-in-part of Ser. No. 634,908, Nov. 14, 1975, Pat. No. 4,034,751.

[51] Int. Cl.$^2$ .................. A61F 13/00; A61L 15/01
[52] U.S. Cl. .................. 128/156; 128/268; 128/334 R; 428/159; 428/167; 428/304; 428/447
[58] Field of Search ............ 428/158, 172, 255, 292, 428/247, 447, 236, 231, 448, 188, 224, 376; 264/166, 243, 174, 175, 313, 316, 171, 173, 37, 317, 324, 128, 336, 337, 344, 334; 128/156, 155, 157, 149, 268, 334 R; 156/77, 155

[56] References Cited

U.S. PATENT DOCUMENTS

| 2,813,052 | 11/1957 | Lancaster | 428/247 |
|---|---|---|---|
| 3,099,067 | 7/1963 | Merriam et al. | 264/128 |
| 3,132,194 | 5/1964 | Edmonds, Jr. et al. | 264/37 |
| 3,264,155 | 8/1966 | Rhee | 428/230 |
| 3,310,505 | 3/1967 | Parker | 260/2.5 |
| 3,382,309 | 5/1968 | Breen | 264/171 |
| 3,397,106 | 8/1968 | Moseley, Jr. | 428/172 |
| 3,455,306 | 7/1969 | Spanel | 428/230 |
| 3,457,919 | 7/1969 | Harbard | 428/167 |
| 3,562,374 | 2/1971 | Okamoto et al. | 264/128 |
| 3,648,692 | 3/1972 | Wheeler | 128/156 |
| 3,762,978 | 10/1973 | Holmes et al. | 428/448 |
| 3,783,093 | 1/1974 | Gallacher | 156/77 |

FOREIGN PATENT DOCUMENTS 940451 1/1974 Canada ............................ 3/1

OTHER PUBLICATIONS

Burns, W., Biomed. Eng., vol. 4, pp. 356–359, (1969).
Kornberg, et al., Trans. Am. Soc. Artificial Internal Organs, vol. 18, pp. 39–44, (1972).
General Electric Corp., Preliminary Product Data Report, re: RTV-7000, (Mar. 1972).

*Primary Examiner*—Stanley S. Silverman
*Attorney, Agent, or Firm*—Ronald A. Schapira

[57] ABSTRACT

Polymeric sheets having on one or both sides a fabric texture and, optionally, a network of elongated channels in the interior of the structural framework of the sheets. The sheets comprise a plurality of interbonded continuous polymeric ribs extending in a direction parallel to the plane of the sheets. These ribs impart a fabric texture to both sides of the sheets and define between them recessed portions on each surface of the sheets. The elongated channels extend throughout the ribs. The open area between the ribs can vary from zero to 60%. In another embodiment, the sheets have an ultra-thin, pinhole-free polymeric membrane on one side and a fabric texture on the other side. The sheets are useful as burn coverings where they serve as synthetic, temporary replacements for damaged or missing skin. The sheets have physiologic properties similar to human skin, excellent drapability characteristics, recessed portions which provide a reservoir for wound debris and, in certain embodiments, a dermal surface which permits wound adherence by fibrolastic ingrowth.

18 Claims, 33 Drawing Figures

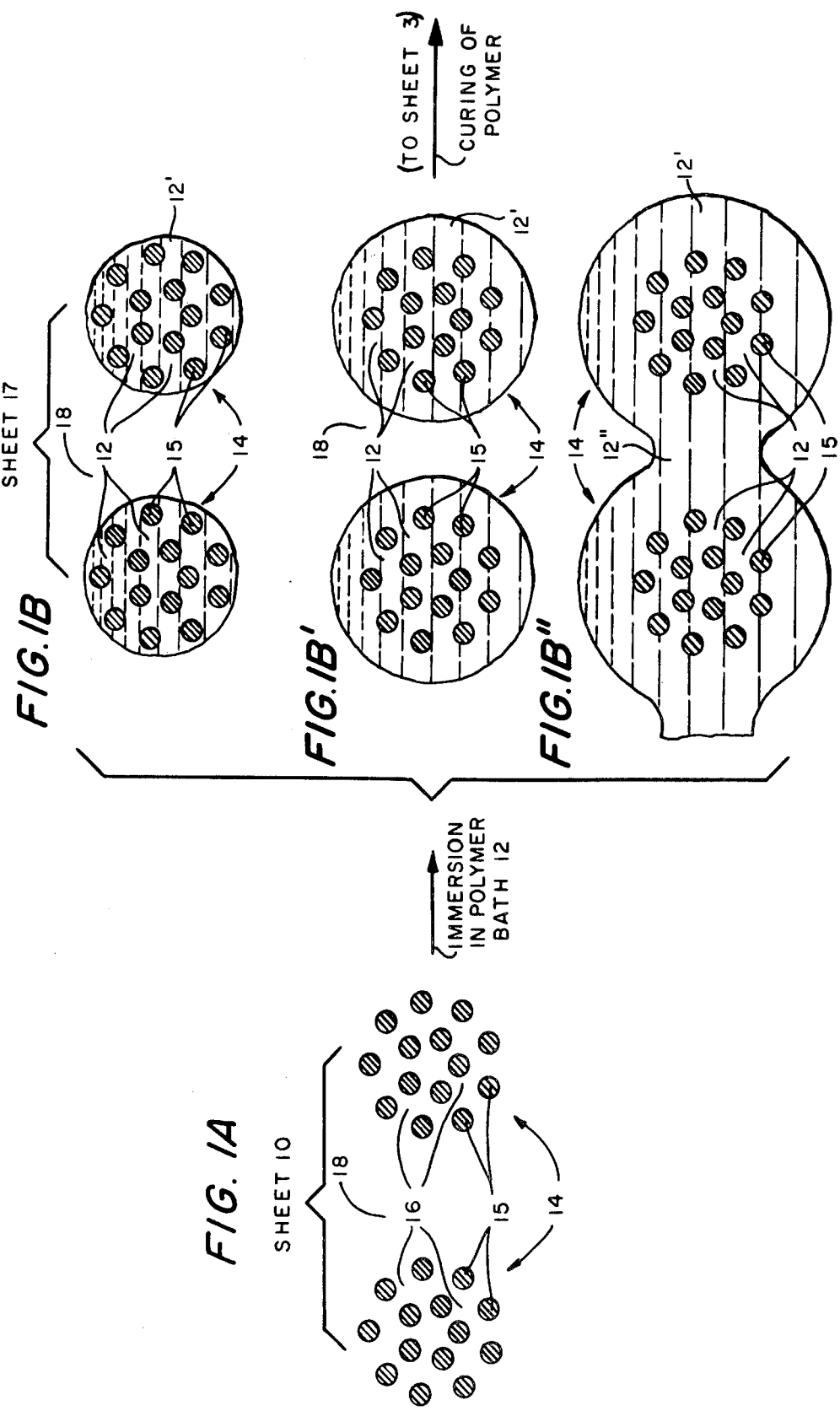

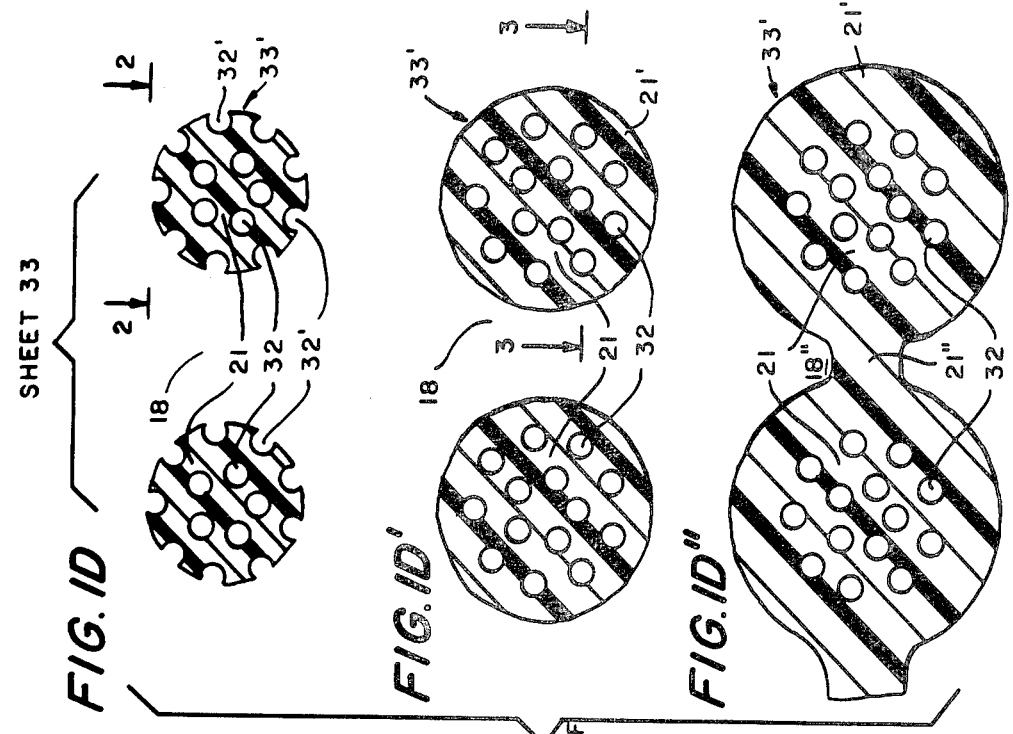

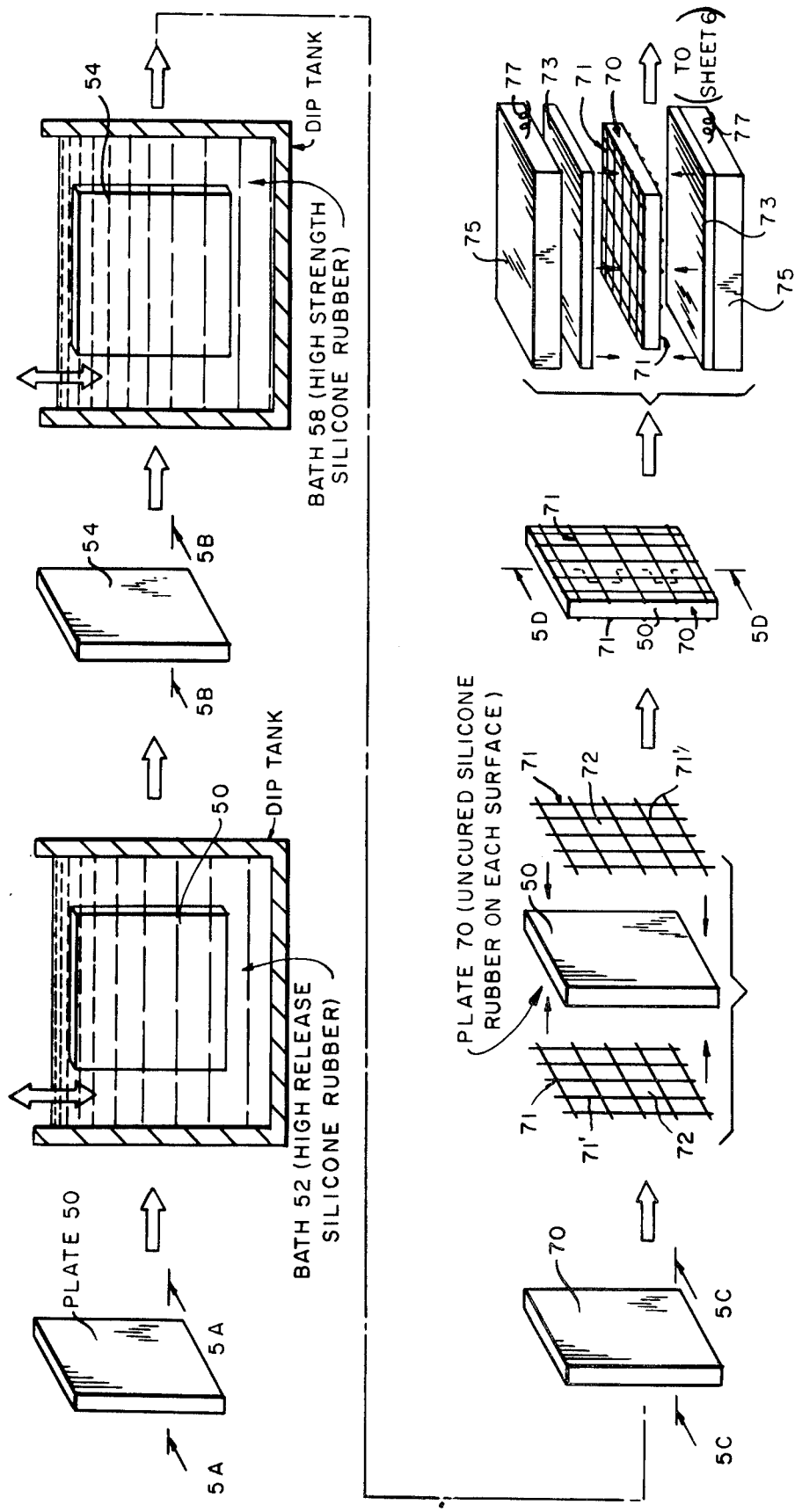

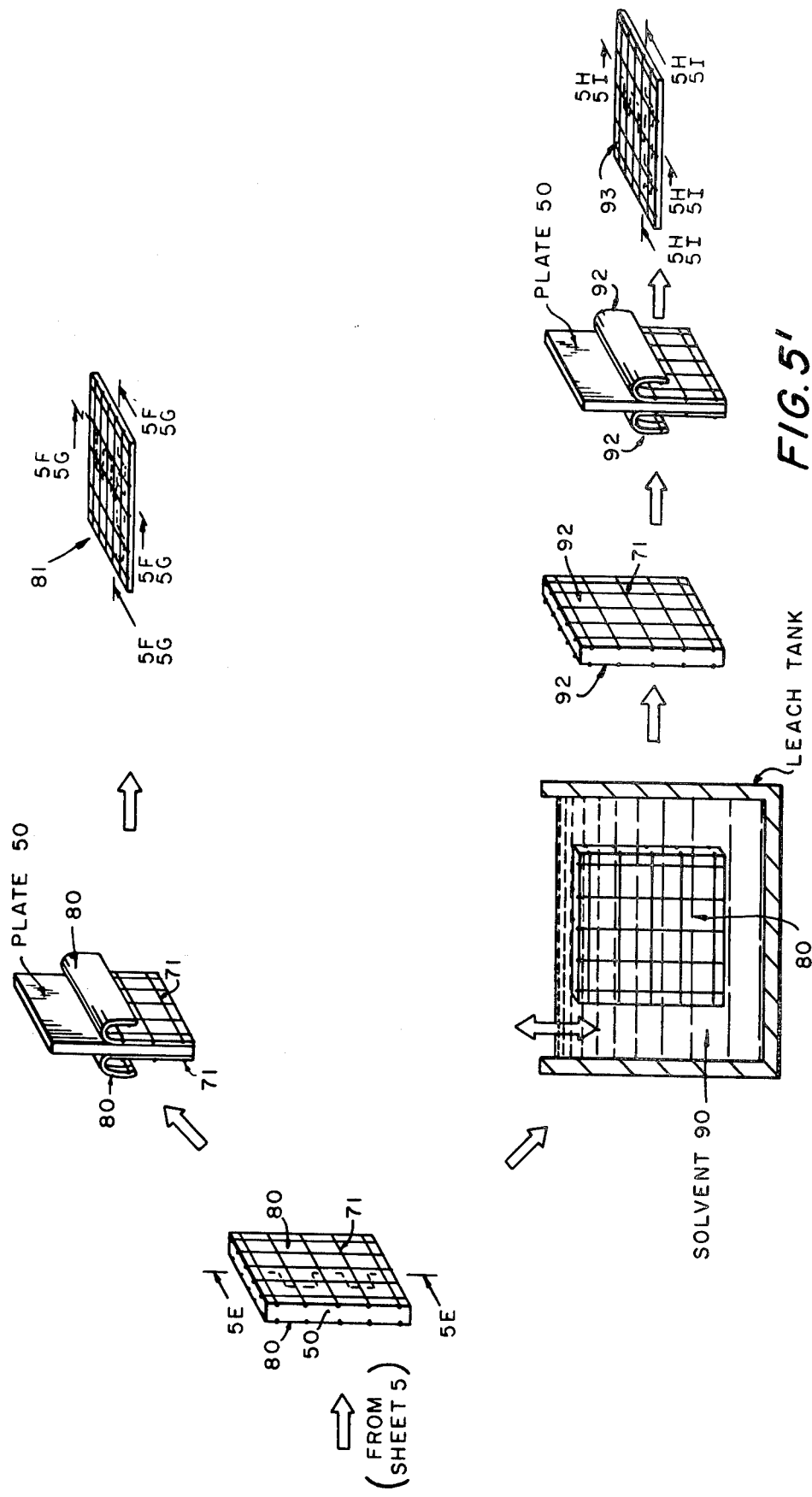

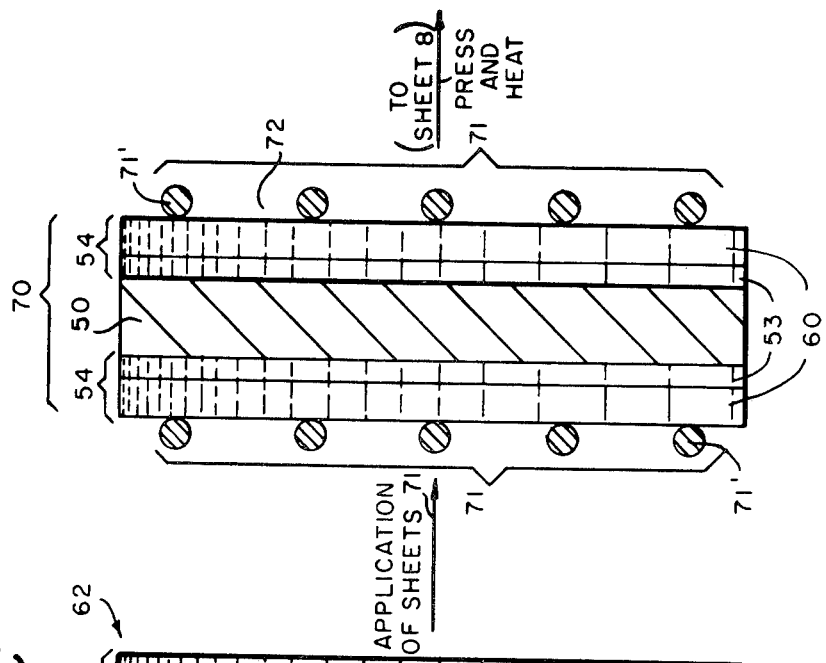
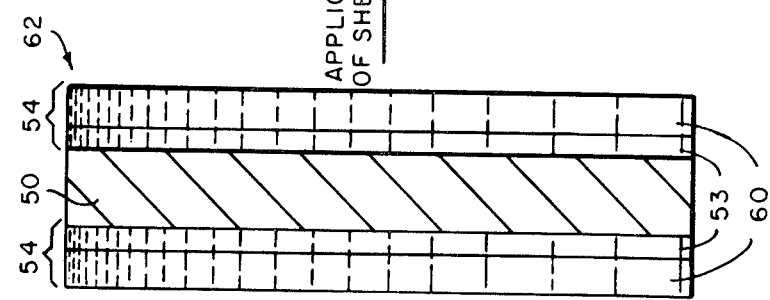
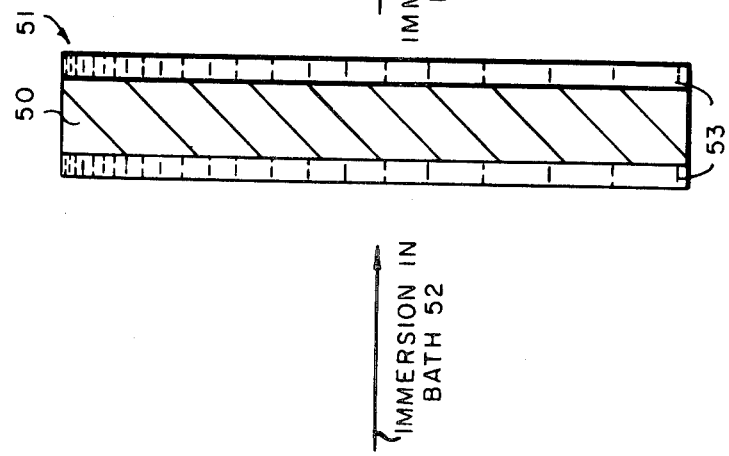
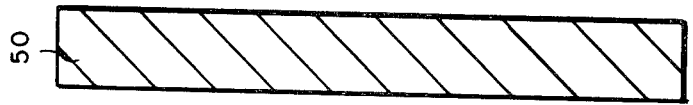

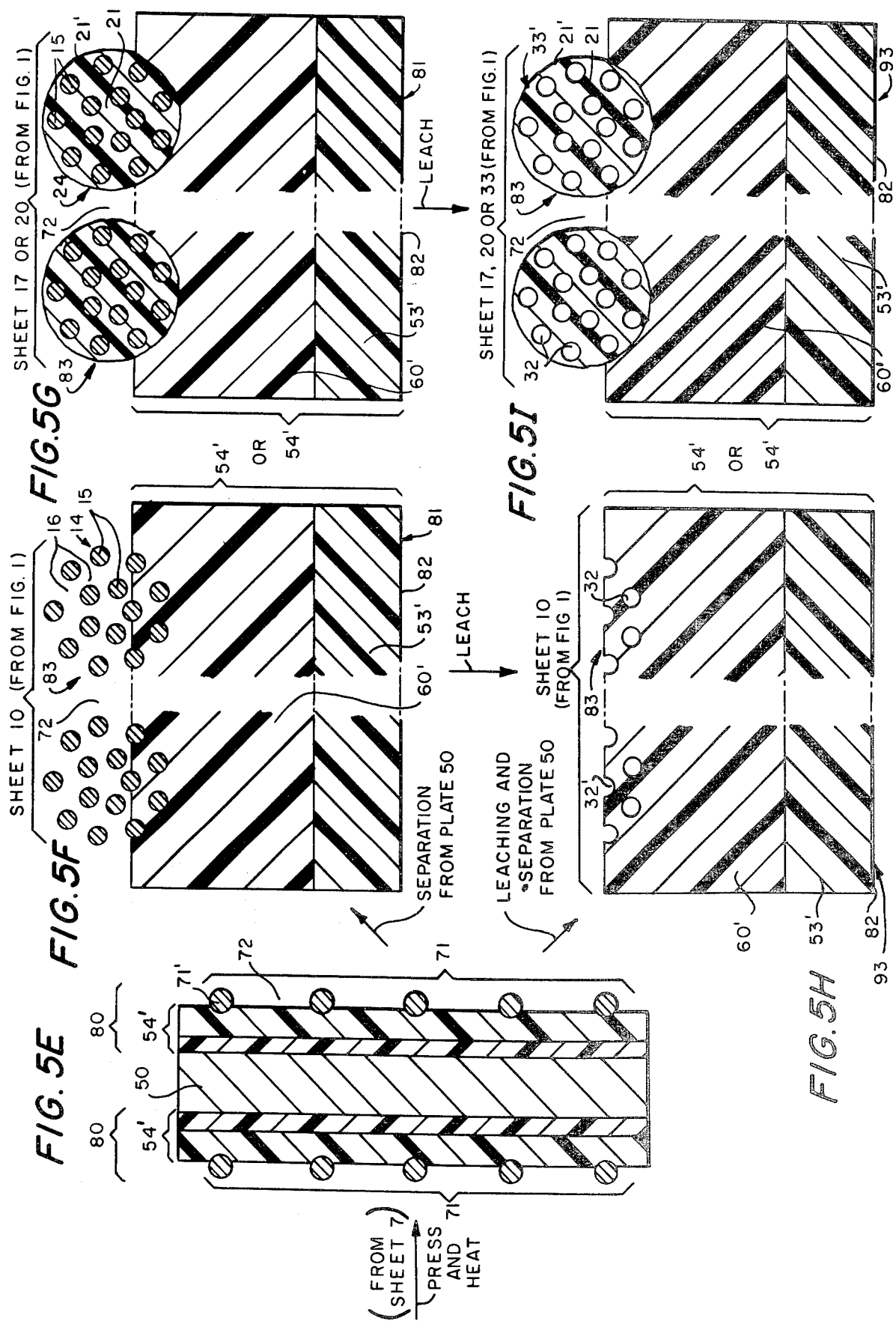

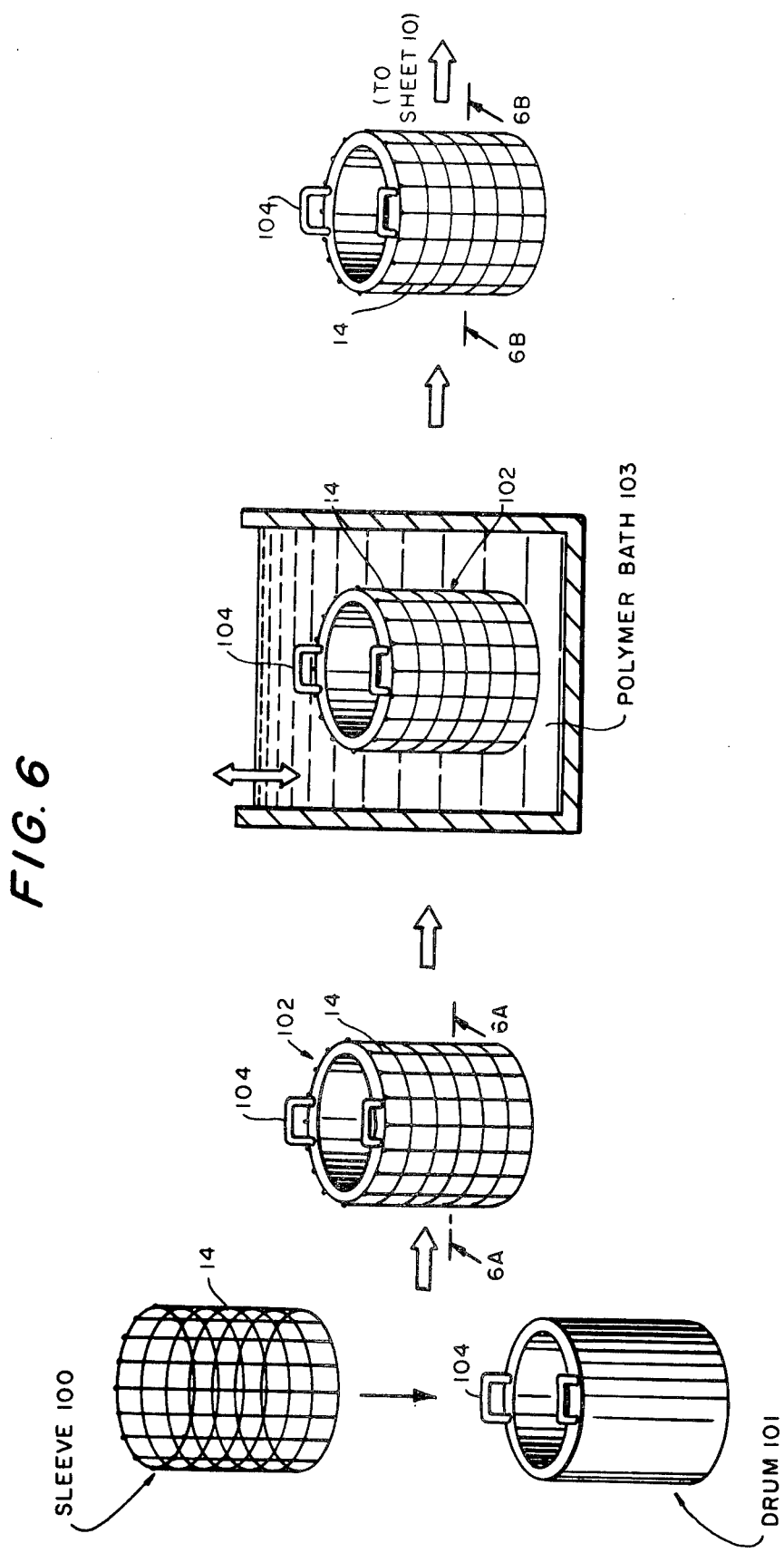

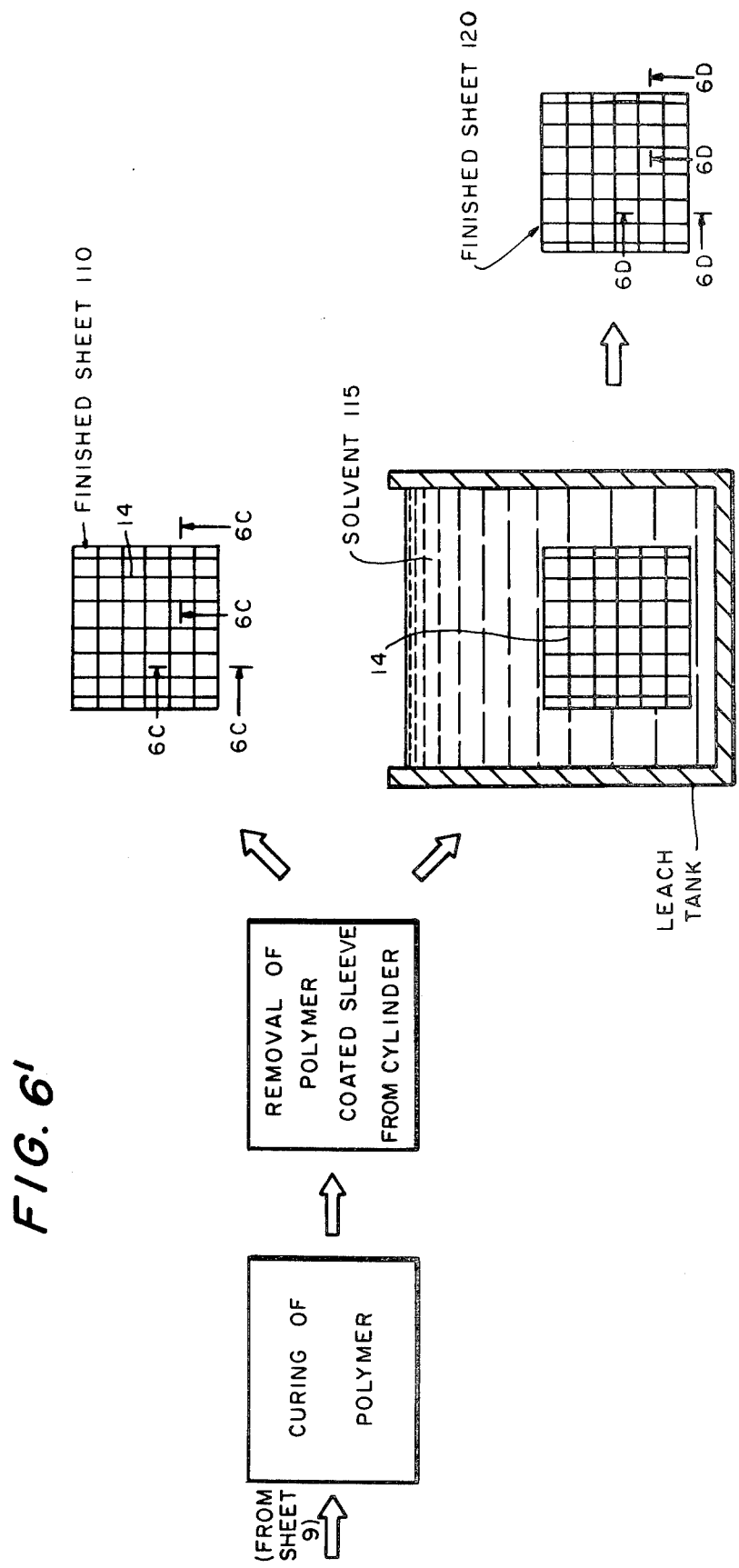

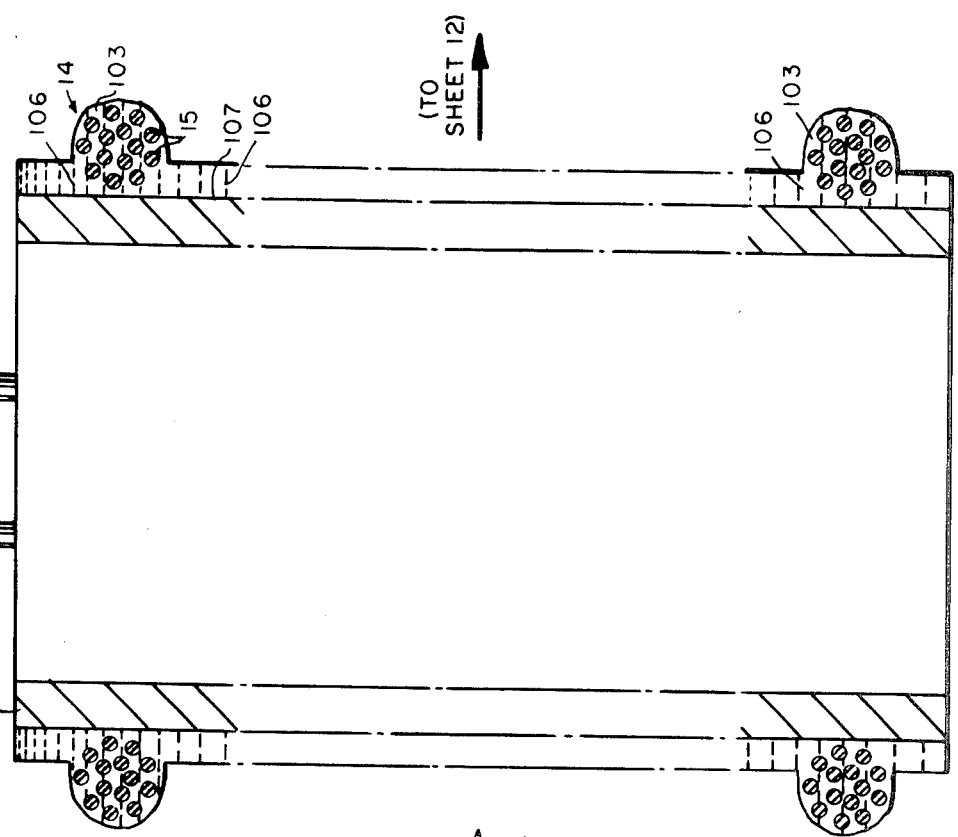
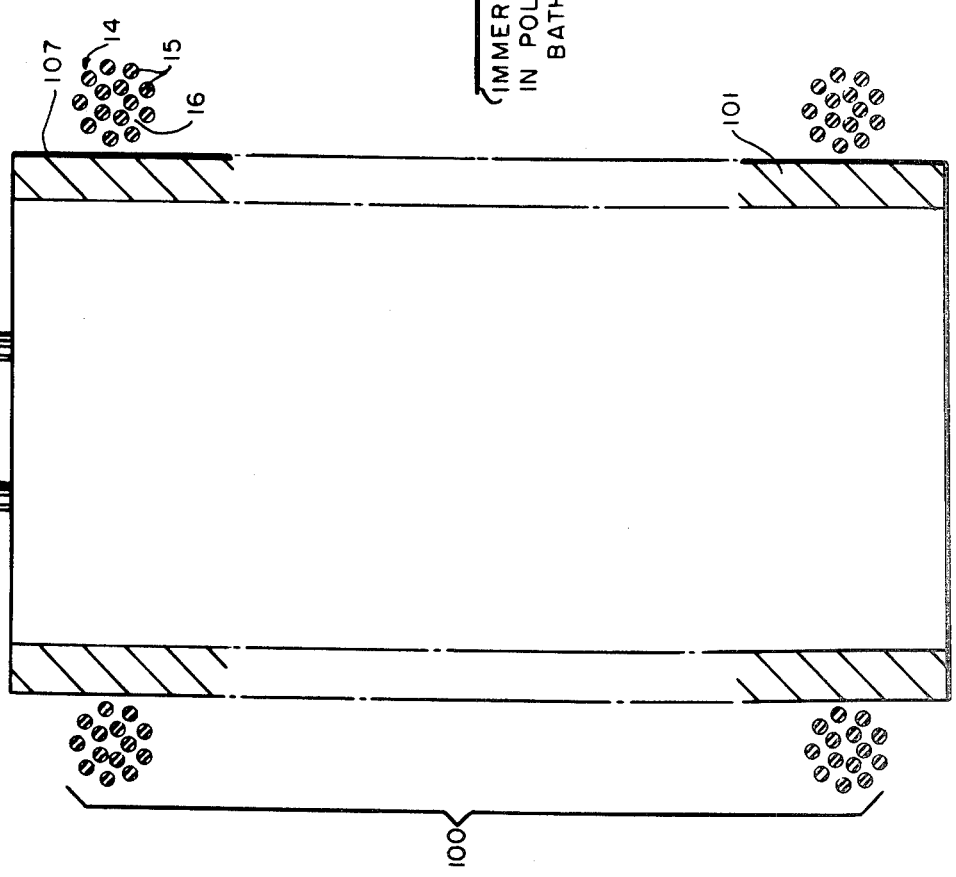

POLYMERIC SHEETS

CROSS REFERENCE TO RELATED APPLICATIONS

This is a continuation-in-part of an application under Ser. No. 634,908, filed Nov. 24, 1975, now U.S. Pat. No. 4,034,751 entitled "Polymeric Sheets."

BACKGROUND OF THE INVENTION

This invention relates to synthetic medical dressings or coverings for wounds and to processing techniques for preparing such dressings or coverings. More particularly, it relates to thin drapable sheets of polymeric material which have physiologic properties similar to human skin plus other desirable properties which made the sheets especially useful in the treatment of thermal wounds, conventionally classified as "burns". The medical problems posed by burn wounds and the general requirements for the successful treatment of such wounds are known to those skilled in the art. See, for example, the discussion in U.S. Pat. No. 3,648,692, entitled "Medical-Surgical Dressing For Burns And The Like", particularly that at column 1, lines 10–69.

The major problem with a burn wound is that the protective layer of skin is either missing or badly damaged at the wound site, so that the normal physiologic functions of the skin are absent or, at best, materially impaired. Two important physiologic functions of the skin are to serve as an antimicrobial barrier layer to prevent infection and to prevent the undue loss of body fluids, proteins and electrolytes. Once the skin can no longer adequately perform these functions, the body fluids, proteins and electrolytes are continuously lost and the invasion of harmful micro-organisms and other harmful agents into the body can proceed with predictable adverse results. For example, normal human skin has a water vapor phase transfer rate of about 2 mg./hr.-cm.$^2$, whereas the rate for burned skin can be 25 to 45 mg./hr.-cm.$^2$ or even higher during the first few hours after the burn. To alleviate these problems, the standard medical treatment for burns involves a combination of therapy and dressing to cover the burn site as soon as possible with a protective layer, the properties of which resemble the burned-away skin. While the use of topical and systemic antibacterial agents can reduce the extent of infection in a burn patient, coverage of the wound site with a skin-like dressing before the onset of infection remains a major factor in burn management.

At the present time, most of the burn dressings used by the medical profession are either human or animal skin. The more common of these dressings are generally referred to as "autografts", "allografts" (also sometimes called "homografts") and "xenografts" (also sometimes called "heterografts"). An autograft is a portion of the burn victim's own skin taken from an uninjured part of the body. The limitations of this dressing are apparent, especially in cases where the victim has suffered extensive dermal destruction. A homograft is skin taken from a cadaver. A xenograft is skin taken from a different species. Pigskin is the most commonly used xenograft. Autografts are generally preferred to homografts and pigskin xenografts.

The various human and animal skin dressings are expensive and are difficult to store for prolonged periods of time. Perhaps the most serious disadvantage of such materials, especially of homografts, is their limited availability. Over 100,000 burn victims are hospitalized in the United States alone every year. While not all such patients require a covering for their burn sites, it is estimated that 50 to 75% of those hospitalized would benefit from such a covering.

Recently, efforts have been made to develop synthetic burn dressings having physiologic properties similar to human skin which could be inexpensively prepared in large quantity and stored for long periods of time without degradation. See, for example, the polyurethane foam burn dressing described in U.S. Pat. No. 3,648,692. Kornberg and his coworkers have described a synthetic burn dressing composed of an ultra-thin (0.5 to 2 mils), pinhole-free silicone rubber membrane, to one surface of which a sheet of spun-bonded nylon, open-weave nylon or double-knit dacron is laminated. See "Ultra Thin Silicone Polymer Membrane: A New Synthetic Skin Substitute", Kornberg, et al., *Transactions of the American Society of Artificial Internal Organs*, Vol. 18, pp. 39–44 (1972). The Kornberg, et al. dressing is impervious to bacteria, inert, non-antigenic, has a water vapor permeability similar to intact human skin, and is transparent and relatively inexpensive to produce.

Much of the success of the Kornberg, et al. dressing is attributed to the work of Nora E. Burns on techniques for mass-producing ultra-thin, pinhole-free silicone rubber membranes for use in membrane oxygenators. This work is described in "Production of Silicone Rubber Film for the Membrane Lung", N. Burns, *Biomedical Engineering*, Vol. 4, pp. 356–359 (1969). Briefly, Burns prepares her ultra-thin silicone rubber membranes by applying an extremely thick dispersion of silicone rubber to a moving horizontal surface and spreading the dispersion into a film of uniform thickness using an accurately ground doctoring blade. Major processing problems generally arise because of the extreme thinness of the silicone rubber membrane, which makes it very difficult to handle without damaging it, and the need for uniform thickness in order to obtain uniform properties throughout the membrane and establish satisfactory quality control.

Among the desired properties of a synthetic burn dressing are that it have water vapor phase transfer rates and anti-microbial barrier layer properties approximating those of human skin, that it adhere well to a wound, and that it preferably have voids in the surface applied to the wound for fibroblastic ingrowth of tissue and to serve as a debris reservoir for necrotic tissue and other debris from the wound, so that such materials are removed from the wound. The dressing should also be transparent or translucent, so the progress of the wound can be observed without removing the dressing. Two dimensional elasticity is another desirable property because it permits the dressing to expand and contract if applied to an elbow, knee or other body location where it is likely that the dressing will be flexed. The dressing should be drapable and readily conform to the shape of the body. It should possess a sufficiently high tensile and tear strength, so that the dressing can be handled and stretched without damage to the dressing. The uniformity throughout the dressing of such properties as the water vapor phase transfer rate and the antimicrobial barrier layer properties is also important, as is control of the characteristics of the dressing which affect these properties. Preferably, the dermal surface has controlled wicking characteristics to remove some but not all the fluid from the wound site, so as to maintain a medically acceptable, balanced fluid level on the wound site, and, of course, the dressing must be constructed from biologically innocuous and inert materials which are acceptable to the medical profession for use with human beings.

It is an object of this invention to provide improved synthetic polymeric wound dressings having the above properties and characteristics.

It is another object of this invention to provide processing techniques for preparing these improved synthetic dressings by which the properties and characteristics of the dressings can be varied in accordance with the contemplated end use of the dressings.

It is another object of this invention to provide improved silicone rubber burn dressings and processing techniques for preparing such dressings.

These and other objects of the invention will be apparent to those skilled in the art upon a consideration of the specification and attached drawings, taken in their entirety.

SUMMARY OF THE INVENTION

The above objectives are accomplished, in accordance with the invention, by providing an integral, continuous, non-foamed, drapable polymeric sheet which can be partly or completely non-woven, non-fibrous and non-filamentary and one or both sides of which have a fabric texture. In one embodiment, the sheet comprises a plurality of interbonded continuous polymeric ribs extending between the thin edges of the sheet which define between them recessed portions in one or both sides of the sheet. These ribs contain a plurality of elongated continuous channels of a filamentary configuration interiorly located therein, which also extend between the thin edges of the sheet to form a network of voids within the ribs. In another embodiment, the sheet comprises an ultra-thin polymeric membrane layer, one side of which has a fabric texture.

The polymeric sheet of the invention has a water vapor phase transfer rate of about 2 to 20 mg./hr.-cm.$^2$, two dimensional elongation of at least about 100% in each direction, an open area of zero to about 60%, and numerous other properties desirable in a wound or burn dressing. All water vapor phase transfer rate data herein are at 37° C. and 46% relative humidity.

A polymeric sheet having a fabric texture on both sides is prepared by applying a polymer to the surfaces of a skeleton sheet having a fabric texture on each surface, the polymer being different from the material of the skeleton sheet, curing the polymer on the skeleton sheet, and treating the composite of polymer and skeleton sheet with a solvent in which the skeleton sheet but not the polymer is soluble. The solvent selectively leaches the skeleton sheet out of the composite, leaving only a polymeric sheet having substantially the surface contour of the skeleton sheet and containing a network of voids conforming to the configuration of the solids portion of the leached skeleton sheet.

Preferred skeleton sheets include weaves, knits and meshes of continuous multifilament strands of varying percent open area. The polymer impregnates the voids between the individual filaments in each strand and builds up a coating of polymer around each strand until the skeleton sheet is thoroughly impregnated with and substantially encased within a shell of polymer. This shell becomes the polymeric sheet of the invention upon removal of the skeleton sheet.

A polymeric sheet having a fabric texture on one side only is prepared by joining one surface of the polymeric sheet just described to a suitable substrate layer at a point in the preparation of the polymeric sheet either before or after leaching out the skeleton sheet. If done before the skeleton sheet is leached, the polymer on the skeleton sheet can be cured before or after joining to the substrate. An ultra-thin membrane (about 0.2 to 2 mils) of silicone rubber is one example of a suitable substrate layer.

Another embodiment of a polymeric sheet having a fabric texture on only one side comprises an ultra-thin, pinhole-free, substantially non-porous and voids-free membrane layer of a polymer, which preferably is a composite of (1) a non-sticking, high-release polymer and (2) a high strength polymer, to one surface of which is joined a sheet having a fabric texture. This fabric-textured sheet optionally can contain elongated channels and voids located in the interior of its structural framework and can be made of a polymer or different materials. In the polymeric sheet, the polymer of the membrane layer, as well as of the fabric-textured sheet, can suitably be a silicone rubber and, for many applications, is preferably the same silicone rubber.

A polymeric sheet having an ultra-thin polymer membrane on one side only is prepared by applying one or more successive layers of a polymer to a smooth forming surface, embedding one surface of a sheet having a fabric texture in the polymer layer, curing the polymer to form a composite of the sheet and the polymer, and removing the composite from the support surface. If the embedded sheet contains one or more materials other than the polymer, as many of these materials as desired can be leached out of the composite by appropriate selection of a leaching solvent at any convenient point in the processing, as described above.

A further embodiment of a polymeric sheet having a fabric texture on only one side comprises a non-laminated continuous sheet of polymer having on one side thereof an ultra-thin, pinhole-free membrane layer and on the other side a fabric texture formed by portions of the polymer which project from the membrane layer. This polymeric sheet also contains embedded therein a skeleton sheet of a material other than the polymer which has a fabric texture conforming to that of the sheet. If desired, the skeleton sheet can be removed by treatment with a solvent which dissolves the skeleton sheet but not the polymer, to thereby create a plurality of elongated continuous channels, interiorly located within the polymeric sheet, which extend in a direction generally parallel to the plane of the sheet and form a network of voids within the sheet.

This non-laminated polymeric sheet is prepared by applying a skeleton sheet having a fabric texture on at least one surface to a backing surface to form a composite of the skeleton sheet and backing surface. In a preferred embodiment, for example, a sleeve of multifilament yarn fabric is placed over the outer surface of a smooth cylindrical drum and then circumferentially stretched on the drum. A liquid containing a polymer such as silicone rubber is subsequently applied to the skeleton sheet while it adjoins the backing surface. The polymer coats the surfaces of the skeleton sheet and forms an ultra-thin layer between the skeleton sheet and the backing surface. The polymer is then cured, and the sheet of cured polymeric material containing the embedded skeleton sheet is removed from the backing surface. The skeleton sheet can be removed, if desired, as described above, by treatment with a selective solvent for the skeleton sheet. A principal advantage of this mode of sheet preparation is that the final product is entirely non-laminated, being formed of a continuous polymer phase. One surface of the polymeric sheet is an ultra-thin membrane while the other surface is formed by portions of polymer projecting from the membrane layer. These projecting portions, however, are continuous with the membrane and thus cannot delaminate or otherwise separate from the membrane.

The sheets of the invention can be fabricated with substantially uniform physiologic properties appoximating those of human skin. They have excellent strength and two-dimensional elongation characteristics and can be fabricated from biologically inert and medically acceptable materials such as silicone rubber. The texture of at least one surface of each sheet provides a reservoir for wound debris, so that the debris does not remain in place on the wound site. The sheets are transparent or translucent, easy to handle, and can be stably stored for prolonged periods of time. Their drapability and conformability characteristics are excellent. Because the sheets are prepared from readily available synthetic materials, they can be made available in abundant supply.

The sheets of the invention and the processing techniques for preparing them are described in greater detail below, in conjunction with the accompanying drawings and the description of the preferred embodiments of the invention.

BRIEF DESCRIPTION OF THE DRAWINGS

FIGS. 1A–1D are enlarged sectional views taken generally along the lines 1A–1D in FIG. 1, with background structure eliminated for clarity of illustration.

FIGS. 1B', 1B", 1C', 1C", 1D' and 1D" are enlarged views similar to FIGS. 1B–1D illustrating variations in the extent of polymer build-up on the multifilament strands of FIG. 1A.

FIGS. 5 and 5' are a schematic flow sheet of another preferred embodiment of the invention, showing the preparation of a polymeric sheet having a coarse fabric texture on one surface only and optionally containing elongated channels in the interior of the sheet at the fabric side.

FIGS. 5A–5I are enlarged sectional views taken generally along the lines 5A–5I of FIGS. 5 and 5' with background structure eliminated for clarity of illustration. FIGS. 5F–5I are even more enlarged than FIGS. 5A–5E.

FIGS. 6 and 6' are a schematic flowsheet of still another preferred embodiment of the invention, showing the preparation of a non-laminated polymeric sheet having a coarse fabric texture on one surface only and optionally containing elongated channels in the interior of the sheet at the fabric side.

FIGS. 6A–6D are enlarged sectional views taken generally along the lines 6A–6D of FIGS. 6 and 6', with background structure eliminated for clarity of illustration. FIGS. 6C–6D are even more enlarged than FIGS. 6A–6B.

Figure 1:
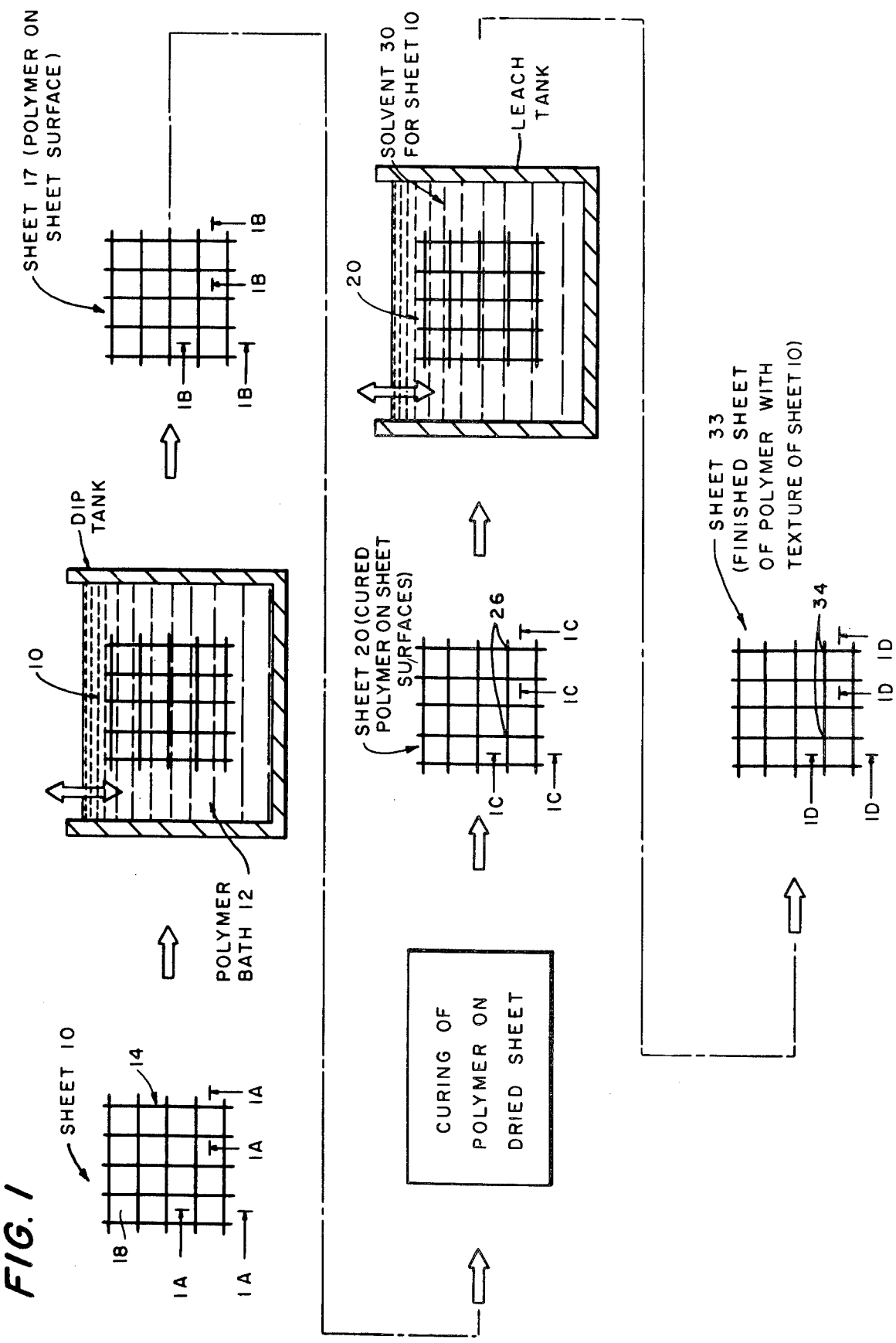
FIG. 1 is a schematic flow sheet of a preferred embodiment of the invention, showing the preparation of a polymeric sheet having a fabric texture on each surface and containing elongated continuous channels in the interior of the sheet.

None of the drawings is drawn to scale or blueprint specification. This is particularly true of FIGS. 5C to 5I and 6A to 6D, where the thickness of the membrane layers 54, 54' and 111 is greatly enlarged for clarity of illustration.

FIGS. 5 and 5' occupy sheets 5 and 6 of the drawings and are best viewed by placing sheets 5 and 6 end-to-end along their short dimension, with sheet 6 to the right of sheet 5.

FIGS. 5A to 5I occupy sheets 7 and 8 of the drawings and are best viewed by placing sheets 7 and 8 end-to-end along their short dimension, with sheet 8 to the right of sheet 7.

FIGS. 6 and 6' occupy sheets 9 and 10 of the drawings and are best viewed by placing sheets 9 and 10 end-to-end along their short dimension, with sheet 10 to the right of sheet 9.

FIGS. 6A to 6D occupy sheets 11 and 12 of the drawings and are best viewed by placing sheets 11 and 12 end-to-end along their short dimension, with sheet 12 to the right of sheet 11.

DESCRIPTION OF THE PREFERRED EMBODIMENTS

The polymeric sheets of the invention are readily understood by a consideration of the processes by which they are prepared.

Polymeric Sheet With A Fabric Texture On Both Surfaces

Referring to FIG. 1, the initial starting material is a sheet 10, preferably having a coarse uneven fabric texture on both sides thereof. Sheet 10 serves as a skeleton or superstructure to carry the polymer from which the sheet of the invention is ultimately formed until such time as the polymer on the skeleton sheet can be cured, rigidified, hardened or otherwise rendered self-supporting. Thereafter, skeleton sheet 10 is removed by solvent leaching or other suitable techniques, leaving an integral, self-supporting polymeric shell generally conforming in shape to the leached skeleton sheet and containing elongated channels or voids formed by the removal of sheet 10.

Skeleton sheet 10 can be of virtually any type of construction, e.g., woven, knit, molded, mesh, gauze, netting, expanded, etc., provided it has a fabric texture on both sides. Thus, for example, sheet 10 can be woven or knit fabric formed of monofilament or multifilament yarn strands. The mesh weave shown schematically in FIG. 1 is for purposes of illustration only. Other conventional weaves and knits, such as, for example, the weft knit construction shown in FIG. 9 of U.S. Pat. No. 3,463,158, also provide suitable skeleton sheets.

Preferably, skeleton sheet 10 is composed of a plurality of continuous multifilament yarn strands 14 (see FIG. 1) in which the individual continuous filaments 15 (see FIG. 1A) forming each strand can be twisted, braided, plaited, laid parallel, or in any other suitable construction. Generally, the axes of strands 14 and filaments 15 are substantially parallel to the plane of sheet 10, with the strands 14 and filaments 15 extending from edge to edge of sheet 10.

The thickness of the skeleton sheet can vary widely, depending largely upon the thickness and other properties and characteristics, such as the water vapor phase transfer rate, desired in the finished polymeric sheet.

Illustrative thicknesses of sheet 10 are about 2 to 50 mils, preferably about 5 to 30 mils, particularly about 10 to 30 mils, and quite particularly about 20 to 30 mils.

The amount of open area in the skeleton sheet 10 also can vary widely depending on the extent of open area and other properties and characteristics, such as the water vapor phase transfer rate, desired in the finished polymeric sheet. Illustratively, sheet 10 has an open area of zero to about 60% and preferably about 10 to 50%.

The thickness of the multifilament strands 14 making up skeleton sheet 10 and the number and size of the individual filaments 15 in each strand also can vary considerably depending largely upon the overall thickness of the finished sheet and the number and size of the elongated channels desired in the sheet. For example, the multifilament strands 14 can vary from about 2 to 100 or more individual filaments per strand having diameters of about 0.1 to 5 mils or more. Preferably, the multifilament strands 14 are less than about 20 mils in diameter and contain 10 to 50 individual filaments 15 with diameters ranging from 0.5 to 2 mils. When sheet 10 is composed of monofilament strands, each monofilament is illustratively about 1 to 50 mils in diameter and preferably less than about 20 mils in diameter.

The choice of material from which the skeleton sheet 10 is made is based on the ability of the material to dissolve in a solvent in which the polymer applied to it is substantially insoluble. Consequently, numerous materials can serve as sheet 10. Some illustrative materials for sheet 10 include cellulose; cotton; rayon; silk; linen; polyamides such as nylon, including nylon velours, polyesters such as Dacron; polyacrylonitriles such as Orlon or Creslan; halogenated polyalkylenes such as tetrafluoroethylene, Teflon, Kel-F, and FEP; polyalkylenes such as polyethylene and polypropylene; polyvinylalcohols; polyvinylacetates; polyglycolic acid; polylactic acid; metals such as stainless steel; and the like. Sheet 10 is preferably fabricated from a polymeric medically-acceptable material such as nylon.

Skeleton sheet 10 is mounted on a suitable frame (not shown). If sheet 10 is a biaxially stretchable fabric such as a woven or knit mesh, it is desirable to biaxially stretch it somewhat on the frame to the extent of about 5 to 75% in each direction. Stretching sheet 10, while preferred, is not mandatory.

The stretched skeleton sheet 10 is then immersed one or more times in a bath 12 which can be a solution, dispersion or other suitable form of the polymer from which the finished polymeric sheet is to be formed, for a time sufficient to cover sheet 10 with polymer to the extent desired. FIG. 1A is a greatly enlarged cross-sectional view of the individual multifilament strands 14 in sheet 10 prior to their immersion in bath 12. Strand 14 is composed of a plurality of individual monofilaments 15 which are separated from each other by void spaces 16. As sheet 10 is immersed in the bath 12, the solution or dispersion of polymer impregnates, penetrates and fills the voids 16 and covers or coats the surfaces of the individual filaments 15 as shown in FIGS. 1B to 1B″. The extent to which the strands 14 are also covered or coated by polymer depends upon such factors as the concentration of polymer in the bath and the residence time and number of dips of sheet 10 in the bath. Thus, the amount of polymer build-up on sheet 10 can be controlled to produce as thick or as thin an encapsulating coating 12′ of polymer dispersion or solution 12 as desired on strands 14, as shown in FIGS. 1B to 1B′. This allows the open area of sheet 10 to be reduced as much as desired or even totally eliminated (see FIG. 1B″), depending on how much polymer is applied to sheet 10. FIGS. 1B to 1B″ show the progressive reduction of the open space 18 between strands 14 until, in FIG. 1B‴, space 18 is totally eliminated and replaced by a bridge 12″ of solution or dispersion between adjoining strands 14.

The particular polymer which is selected for application to skeleton sheet 10 depends largely upon the characteristics and properties desired in the finished polymeric sheet. Any of the numerous polymers which have heretofore been used in or disclosed for use in medical and surgical dressings, bandages or other medical products and applications can be employed as coating polymers for sheet 10. These polymers are well known to those skilled in the art and need not be repeated in detail herein. Some illustrative polymers include polyurethanes, polyethylenes, polypropylenes, natural rubber, polybutadiene, silicone rubber and other synthetic and natural elastomeric polymers, such as those of isoprene, neoprene, chlororoprene, styrene-butadiene and various copolymers of the above.

Silicone rubbers are preferred polymers for application to skeleton sheet 10. Silicone rubbers are composed of high molecular weight linear polysiloxanes, such as polydimethylsiloxane and other polysiloxanes in which the methyl groups are replaced by groups such as ethyl, phenyl, vinyl and others. A wide variety of useful silicone rubbers of widely varying properties, chemical compositions and cure properties and characteristics are available commercially from suppliers such as General Electric Co., Dow Corning Corp. and Union Carbide Corp. See, for example, the silicone rubbers disclosed in "The Science and Technology of Silicone Rubber" by F. M. Lewis, *Rubber Chemistry and Technology*, Vol. XXXV, No. 5, December 1962 (pp. 1222–1275), said publication being incorporated herein by reference. Other silicone rubbers are disclosed in U.S. Pat. Nos. 3,334,067, 3,592,795 and 3,708,467 and in the numerous patents on silicone rubbers assigned to the above-mentioned three suppliers, said patents being incorporated herein by reference.

Preferred silicone rubbers for use in bath 12 are those which cure at or close to room temperature to produce transparent films and which, when cured, have a tensile strength for a 25 mil thick film of at least about 400, preferably at least about 700, especially at least about 750, pounds per square inch and a tear strength for a 25 mil thick film of at least about 20, preferably at least about 25, especially at least about 75, pounds per inch. Among such silicone rubbers, especially preferred are the silicone rubbers available under the trade designations RTV-615 and RTV-7000 (now discontinued) and the equivalents thereof from General Electric Co., Schenectady, N.Y. and the silicone rubbers available under the trade designation MDX-4-4210 Elastomer from Dow Corning Corp., Midland, Michigan.

The polymer can be provided in bath 12 as a solution, dispersion, or the like by mixing the polymer with an organic solvent. In bath 12, any conventional inert organic solvent or mixture thereof can be utilized. Among the solvents which can be used are: the straight chain, branched chain, and cyclic aliphatic hydrocarbon solvents, such as pentane, hexane, heptane and cyclohexane; the aromatic hydrocarbon solvents, such as xylene, toluene and benzene; methylethylketone; and tetrahydrofuran. Where the polymer is a silicone rubber, bath 12 is preferably formed as a dispersion of the silicone rubber in a hydrocarbon solvent such as hexane. The concentration of polymer in bath 12 can vary widely, e.g., from about 10 to 60%, depending upon factors such as the extent of polymer pick-up desired and the type of polymer used.

Once skeleton sheet 10 has picked up a sufficient amount of bath 12 to permeate the voids 16 between the individual filaments 15 in each strand of sheet 10 (see FIGS. 1A–1B) and build up as thick a coating 12' as desired on strand 14 (contrast FIGS. 1B–1B''), the polymer treated sheet 17 is then removed from the bath 12 and preferably air-dried for 15 minutes to two hours to remove part of the solvent and increase the polymer concentration on sheet 17. The air-drying step is optional and could be omitted if desired.

If the skeleton sheet is dipped in bath 12 more than one time, it is preferable to air-dry the dipped sheet, as described above, or use other drying techniques prior to each subsequent dip and again after the final dip.

Sheet 17, air-dried or otherwise, is then subjected to conditions which will cure the polymer. The term "cure" as used herein means the conversion of the polymer from a low viscosity form, such as a solution or dispersion wherein the polymer is not self-supporting, to a significantly more viscous or solid form in which it is self-supporting. Curing is generally a "time at temperature" phenomenon, with shorter times required at higher temperatures and longer times at lower temperatures. Conditions for curing the common polymers are well known to those skilled in the art and need not be repeated in detail herein. In general, most polymer curing conditions involve treatments at room temperature (23° C.) to about 200° C. for about 15 minutes to 48 hours. A silicone rubber film of MDX-4-4210 Elastomer, for example, will cure in about 24 hours at room temperature, in about 30 minutes at 75° C., and in about 5 minutes at 150° C. Thick films may take longer to cure than thin films.

If the skeleton sheet 10 is dipped into bath 12 more than one time, the polymer optionally can be dried and/or cured or partially cured after each dip, as well as after the final dip. Any combination of drying alone or drying plus curing could also be employed after each dip.

FIGS. 1C–1C'' show the condition of the multifilament strands 14 in the cured sheet 20 for the three different loadings of polymer depicted in FIGS. 1B–1B''. The cured or hardened polymer 21 is located in the void spaces 16 (see FIG. 1A) between the individual monofilaments 15, and it forms a shell 21' around the strands 14, the thickness of which depends upon how much polymer was applied to strands 14 in bath 12. FIG. 1C'' depicts the condition where the skeleton sheet picked up enough polymer on adjoining strands 14 to form a bridge 21'' of cured polymer between the adjoining strands 14, which totally fills in the open space 18 that existed between the strands 14 prior to the immersion of skeleton sheet 10 in bath 12. At this point in the processing, the sheet 20 comprises a plurality of polymeric ribs or struts 24 interbonded at points 26 (see FIG. 1), which may or may not also be interbonded along substantially their entire length and which contain a multifilament core strand 14 of the skeleton material.

The sheet 20 of cured polymer is then immersed in a bath 30 of a material which is a solvent for the material from which the skeleton sheet 10 is made but not for the polymer 21, 21', 21''. Solvents for the normal materials from which sheet 10 is fabricated are well known to those skilled in the art. For example, formic acid, hydrochloric acid and phenol are well known solvents for nylon, a preferred material for the skeleton sheet. The solvent dissolves out the individual filaments 15 which formed the skeleton or super-structure of the cured sheet 20, leaving a plurality of elongated continuous channels or voids 32 interiorly located in the structural framework of the finished polymeric sheet 33, as shown in FIGS. 1D to 1D''.

In FIGS. 1D' and 1D'', the elongated channels 32 are located within the interior of the polymeric framework of polymeric sheet 33 that is composed of a plurality of polymeric ribs or struts 33' which are interbonded at points 34 (FIG. 1) and which may (FIG. 1D'') or may not (FIGS. 1D and 1D') also be interbonded along substantially their entire lengths. In FIG. 1D'', the ribs 33' are connected by the bridge 21'' of cured polymer, which is of a thinner dimension than ribs 33'. Channels 32 are interiorly located because all the filaments 15 which provided the channels 32 were completely enclosed within a shell 21, 21', 21'' of cured polymer prior to leaching out the individual filaments 15 (see FIGS. 1C' and 1C''). However, in FIG. 1D, the surface of sheet 33 also contains elongated channels 32' similar to channels 32 but which are located exteriorly on ribs 33' instead of interiorly like channels 32. This is because not all the filaments 15 which provided the channels 32 were completely enclosed within a shell of cured polymer prior to leaching out the filaments 15. Thus, note in FIG. 1C that certain of the filaments, designated 15', were still at or close to the surface of the ribs 24 after curing of the polymer. When strands 15' were leached out, they created the elongated voids 32' (see FIG. 1D) in the surfaces of polymeric sheet 33.

The elongated channels both on the surface (channels 32') and in the interior (channels 32) of polymeric sheet 33 generally have the same configuration as the leached solid material from which they were formed. Thus, the network of voids created in sheet 33 by the leaching of the skeleton sheet 10 is an approximate image of sheet 10. Illustratively, channels 32' and 32 are of a continuous filamentary configuration and have a length to diameter ratio of at least 100 and diameters ranging from about 0.1 to 5 mils and preferably from about 0.5 to 2 mils.

The number of channels 32 and 32' present in each rib 33', as well as their total length, internal surface area and volume, can vary considerably depending on such factors as the size and quantity of the precursor filaments 15 and strands 14 from which they were formed. For example, the number of internal channels 32 found in a given rib 33' is illustratively about 10 to 40. The total length of internal channels 32 present in a polymeric sheet 33 can vary widely, e.g., from about 1 to 8 miles of such channels per square foot of sheet. The internal surface area of channels 32 is illustratively about 2 to 10 square feet per square foot of sheet 33. The volume of channels 32 can range from about 1 to 6 cubic centimeters per square foot of sheet, and the channels can occupy about 20 to 60% of the total volume of the sheet. Preferably, the sheets 33 contain about 12 to 35 channels per rib, and the channels have a total length of about 2.5 to 6.5 miles per square foot of sheet, an internal surface area of about 3 to 8.5 square feet per square foot of sheet, a volume of about 1.5 to 4.75 cubic centimeters per square foot of sheet, and occupy about 30 to 52% of the total volume of the sheet.

Figure 2:
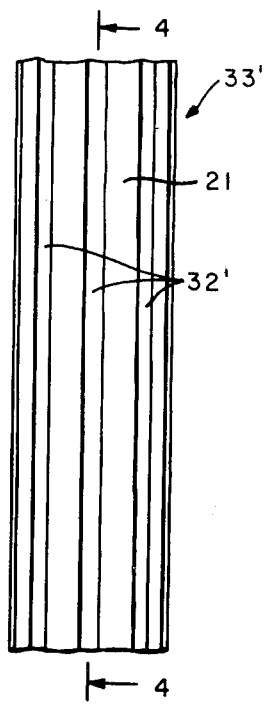
FIG. 2 is an enlarged fragmentary plan view taken generally along the line 2—2 of FIG. 1D.
Figure 3:
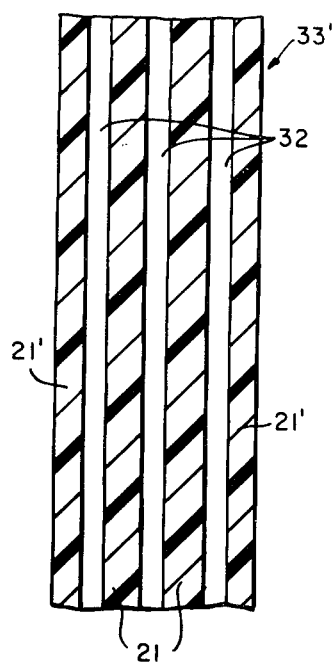
FIGS. 3 and 4 are enlarged fragmentary sectional views taken generally along the lines 3—3 and 4—4 of FIGS. 1D' and 2, respectively.
Figure 4:
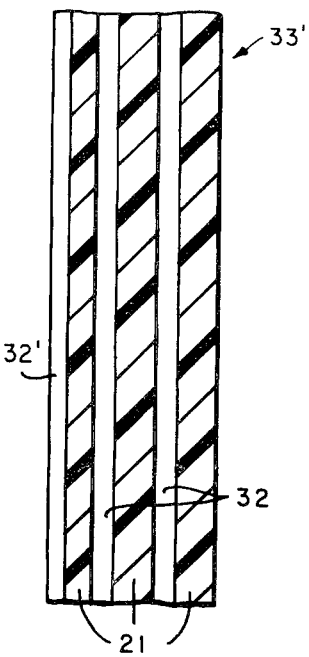
Figure 2:
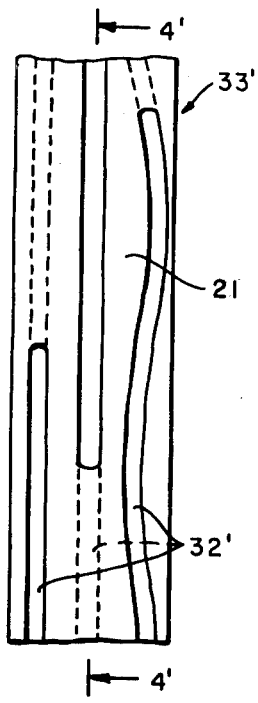
Figure 3:
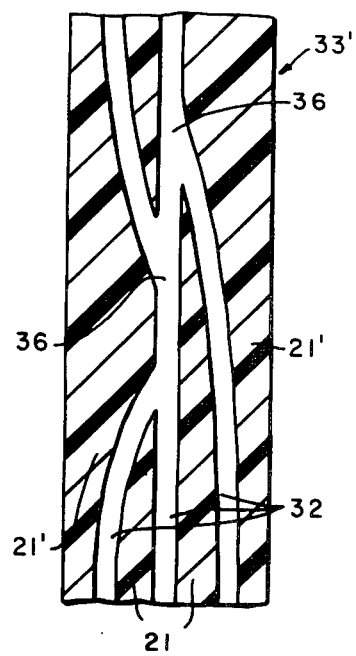
Figure 4:
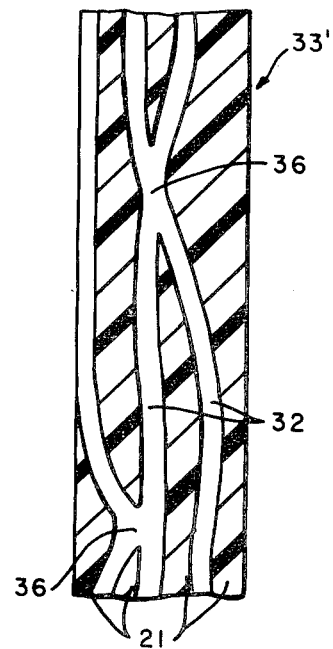
Figure 6C:
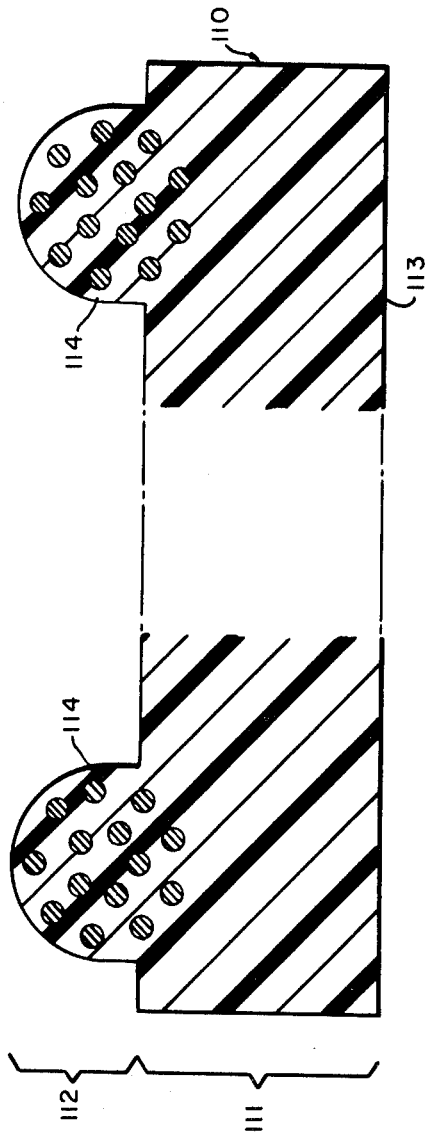
Figure 6D:
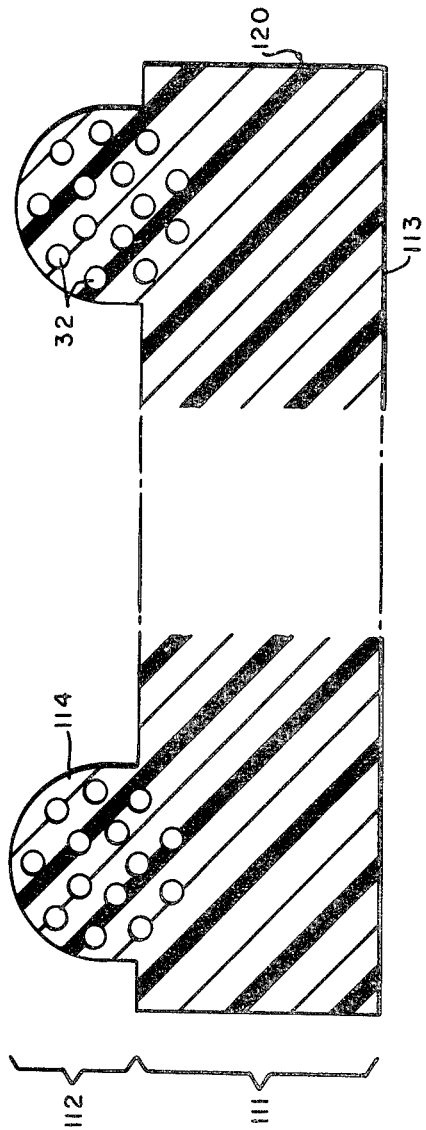

In polymeric sheet 33, channels 32 and 32' can be essentially parallel to each other, as shown in FIGS. 2-4, or they can extend in a random or haphazard fashion, as shown in FIGS. 2'-4'. It is not uncommon, for example, for the surface channels 32' to descend into the interior of the polymeric framework as shown in FIGS. 2' and 4'. Nor is it uncommon for the surface channels 32' or the interior channels 32 to intercommunicate as at locations 36 in FIGS. 3' and 4'. However, the channels 32 and 32' normally extend in a direction generally parallel to the plane of sheet 33, with most of the channels extending between the thin edges of the sheet and not between the two sides or faces of the sheet. This produces a network of voids 32, 32' which is oriented to provide continuous communication between the edges instead of between the faces of the sheet.

As will now be apparent, virtually any type of a network of voids can be built into the polymeric framework of the sheet 33 by appropriate selection of the skeleton sheet 10. For example, the number and size of channels provided is readily controlled by the number and size of the filaments which make up sheet 10. The ability to vary the voids or porosity of polymeric sheet 33 in this fashion can also be utilized to vary properties of the sheet 33 which are related to its porosity, such as its water vapor phase transfer rate and its anti-microbial barrier layer properties.

The elongated channels 32, 32' also provide a reservoir for one or more medicating agents which can be released to a wound covered by the polymeric sheet 33 over a period of time. The channels can be loaded with a medicating agent by immersing sheet 33 in a solution or dispersion of the agent until the desired loading is achieved. The sheet can then be removed from the solution or dispersion and dried if necessary. Illustrative medicating agents include medicines, antibiotics, antiseptics, germicides, antimicrobial agents, and other materials useful in treating wounds or burns. For example, the elongated channels of sheet 33 can be impregnated with PVP-Iodine (polyvinylpyrrolidone-iodine) complex by immersing sheet 33 in a 10% aqueous solution of the PVP-Iodine solids. PVP-Iodine is a water soluble, non-irritating microbiocide with broad spectrum activity and is available from the General Aniline and Film Corp.

Polymeric sheet 33 has a fabric texture on each of its surfaces similar to the texture of the leached skeleton sheet 10 on which it was constructed. This type of surface provides pockets or reservoir spaces to accept the necrotic tissue and other debris from a wound site.

Water vapor phase transfer rates through sheet 33 can be controlled by varying the thickness of sheet 33, the extent of the open area in the sheet and the porosity imparted to the sheet by the elongated channels. Thickness and open area are largely controlled by the thickness and open area of skeleton sheet 10 and the extent of polymer build-up on sheet 10, while porosity is largely controlled by the nature of the skeleton sheet as previously discussed.

Polymeric sheets 33 are integral, continuous, non-laminated, non-woven, non-fibrous, non-filamentary, non-foamed, gauze or mesh-like sheets, preferably formed from a single polymeric entity and having a fabric texture on each side thereof. They have a structural framework comprising a plurality of interconnecting polymeric ribs or struts 33' which are spaced from each other along their length either by open area 18 (FIGS. 1D-1D') or a bridging layer 21" (FIG. 1D") which is thinner than ribs 33'. The ribs 33' define between them recessed portions 18 (in FIGS. 1D-1D') and 18' (in FIG. 1D") in both sides of sheet 33. The ribs 33' contain the elongated, continuous filamentary channels 32, 32' in their interior and, optionally, on their surface, with the axis of most of the ribs and elongated channels being generally parallel to the plane of the sheet 33 and extending between the edges of the sheet.

The size of the ribs 33' can vary widely depending on how they were formed. Illustratively, ribs 33' have a diameter of about 4 to 30, preferably about 5 to 10, mils. The length of the ribs 33' is typically about 650 to 2600, preferably about 975 to 2300, feet per square foot of sheet 33. The outer surface area of the ribs 33' is typically about 1 to 4, preferably about 1.5 to 3, square feet per square foot of sheet 33.

A number of polymeric sheets 33 were prepared using the procedures illustrated in FIG. 1. For example, multifilament nylon (nylon 66) meshes of sizes 1×40 (denier per strand)/13 (filaments per strand), 1×50/13 and 1×50/17, obtained from Hanes Corporation, were stretched on 9¼ inch by 11 inch stainless steel frames and then immersed in a silicone rubber-hexane dispersion (RTV-7000, General Electric Co.). The number of dips in the silicone rubber dispersion and the concentration of solids in the dispersion were varied. Each dip was carried out by immersing the stretched nylon mesh sleeves in the silicone rubber-hexane dispersion and then immediately removing the sleeves from the dispersion at a constant withdrawal rate of about 38 inches per minute. Each sample required about 15 seconds before it was completely withdrawn from the dispersion. Between dips, the coated nylon samples were air dried for about 10 minutes. The silicone rubber on the nylon samples was then cured at about 75° C. for 1¼ hours. The coated nylon samples were then immersed in formic acid at room temperature for about 16 hours or longer to dissolve out the nylon. The silicone rubber sheets which remained were dried, and various physical properties of the finished sheets were then measured. The physical properties measured are shown in Table 1, which follows.

As the data in Table 1 show, polymeric sheets 33 with a wide variation in properties are obtainable. The open area of the sheets 33 can be varied from 0 to about 60%, as desired, and water vapor phase transfer rates of about 2 to 20 mg./hr.-cm.$^2$ or more are obtainable. Preferably, the percent open area is about 10 to 50%, and the water vapor phase transfer rate is about 2 to 10 mg./hr.-cm.$^2$ in order to prevent excessive drying of a wound surface. By varying the thickness and/or extent of open area, varying degrees of transparency can be imparted to the sheets. The sheets have excellent drapability and conformability characteristics and have thicknesses of, for example, about 5 to 30 mils. The sheets elongate easily in both directions by as much as 100% or more and preferably by as much as 200% or more. Illustratively, a 1×3 inch strip will stretch 100% in a direction parallel to the 3 inch dimension at a force of less than about 0.5 pound per inch and will stretch 200% at a force of less than about 1 pound per inch. Typically, a force of about 0.1 to 0.3 pound is required for 100% stretch and a force of about 0.2 to 0.5 pound for 200% stretch.

The particular properties of the polymeric sheets 33 are normally selected in accordance with the desired end use of the sheets. For example, if the sheets are to be used as a burn dressing, a low water vapor phase transfer rate approaching that of human skin would be desired.

TABLE 1
PROPERTIES OF FINISHED SILICONE RUBBER SHEET

| No. of dips x % solids in bath | Average Maximum Thickness (±1 mil) | Weight (gms./ft.[2]) | Necessary Force to Elongate 100% a One-Inch Wide Sample (lbs./in.) | Necessary Force to Elongate 200% a One-Inch Wide Sample (lbs./in.) | % Elongation at Break | Water Vapor Transfer Rate (mg./hr.—cm.[2]) | % Open Area | Total Number of Holes/in.[2] |
|---|---|---|---|---|---|---|---|---|
| 2 × 20% | 9 | 5.17 | 0.1 | — | 160 | 10.0 | 29 | 2058 |
| 3 × 20% | 12 | 9.06 | 0.2 | 0.4 | 230 | 5.5 | 11 | 350 |
| 4 × 20% | 14 | 14.33 | 0.4 | 0.8 | 320 | 3.5 | 2 | 336 |
| 1 × 25% | 10 | 5.51 | — | — | 190 | 13.0 | 42 | 1855 |
| 2 × 25% | 10 | 6.98 | — | 0.2 | 300 | 8.0 | 22 | 1245 |
| 3 × 25% | 16 | 15.96 | 0.5 | 0.9 | 450 | 3.2 | 0 | 0 |
| 1 × 30% | 12 | 7.59 | 0.1 | 0.2 | 250 | 8.8 | 24 | 364 |
| 2 × 30% | 12 | 14.52 | 0.4 | 0.8 | 380 | 4.0 | 0 | 0 |

Additional polymeric sheets 33 were prepared in a manner similar to that just described for the sheets of Table 1, using a variety of different nylon meshes as the extractable components. The nylon mesh samples used were obtained from Hanes Corporation, Amtex, Inc. and Finetex Elastic Corporation. The Hanes sample was identified as a 1×40/13 nylon, as described above. The Amtex sample was identified as Style No. 224-2. The three Finetex samples were identified as #2, #9, and #15.

Each sample of nylon was immersed in a 22% solids dispersion of General Electric RTV-7000 silicon rubber in hexane and then removed from the dispersion, using the procedure described above. The samples were air-dried for 20 minutes and reimmersed in the 22% RTV-7000 silicone rubber dispersion as before. The samples were subsequently air-dried for 20 minutes and cured at 75° C. for two hours. The resulting products were then leached with 88% formic acid for at least 8 hours, after which, the leached products were rinshed in water for 10 minutes and dried at room temperature.

Data on the microchannels 32 and the ribs 33' of the polymeric sheets 33, made in this way, are set forth in Tables 2, 3 and 4, which follow.

TABLE 2
DIMENSIONS OF CHANNELS 32

| Extractable Sleeve Material | Hanes 1×40/13 | Amtex 224-2 | Finetex #2 | Finetex #9 | Finetex #15 |
|---|---|---|---|---|---|
| Average Number of Channels Per Rib 33' | 13 | 28 | 12.5 | 28 | 31.5 |
| Diameter of Channels 32 (mils) | 0.84 | 0.76 | 0.88 | 0.94 | 1.18 |
| Calculated Total Length of Channels 32 (miles/sq.ft.) | 2.68 | 6.47 | 5.63 | 6.50 | 4.84 |
| Calculated Total Internal Surface Area of Channels 32 (sq.ft./sq.ft.) | 3.1 | 6.8 | 6.9 | 8.4 | 7.9 |

TABLE 3
VOLUME OF CHANNELS 32

| Extractable Sleeve Material | Hanes 1×40/13 | Amtex 224-2 | Finetex #2 | Finetex #9 | Finetex #15 |
|---|---|---|---|---|---|
| Volume of Channels 32 (cc/sq.ft.) | 1.55 | 3.02 | 3.57 | 4.66 | 5.44 |
| Total Volume of Sheet (cc/sq.ft.) | 4.86 | 10.07 | 8.31 | 12.94 | 10.46 |
| Silicone Rubber Volume (cc/sq.ft.) | 3.31 | 7.05 | 4.74 | 8.28 | 5.02 |
| Total Sheet Volume Occupied by Channels 32 (%) | 30 | 32 | 36 | 43 | 52 |

TABLE 4
DIMENSIONS OF RIBS 33'

| Extractable Sleeve Material | Hanes 1×40/13 | Amtex 224-2 | Finetex #2 | Finetex #9 | Finetex #15 |
|---|---|---|---|---|---|
| Thickness of Sheet (mils) | 8 | 13 | 13 | 23 | 23 |
| Calculated Diameter of Ribs 33' (mils) | 5.38 | 7.31 | 4.75 | 8.26 | 9.13 |
| Calculated Length of Ribs 33' (ft./sq.ft.) | 1,084 | 1,200 | 2,380 | 1,230 | 811 |
| Calculated Surface Area of Ribs 33' (sq.ft./sq.ft.) | 1.53 | 2.33 | 2.96 | 2.65 | 1.94 |

The process illustrated in FIG. 1 could be readily performed on a continuous basis by advancing a web or continuous strand of the skeleton sheet 10 sequentially through (1) a bath 12 of polymer to coat it with polymer, (2) a curing chamber or oven to cure the polymer on sheet 10, and (3) a leach tank containing a solvent to selectively dissolve sheet 10 but not the cured polymer, and finally (4) a drying chamber to remove solvent from the finished product.

Polymeric Sheet With A Fabric Texture On One Surface Only

FIGS. 5 and 5' depict a process for preparing polymeric sheets having a coarse fabric texture on one side only. The other side or non-fabric side is a pinhole-free, ultra-thin polymeric membrane which is an antimicrobial barrier layer but remains sufficiently permeable to water vapor to permit its usage as a wound dressing. Preferably, the polymeric membrane is composed of silicone rubber. A plurality of filamentary microchannels can be optionally provided at the fabric side of the sheet.

Briefly, polymeric sheets of this type are prepared by forming the ultra-thin membrane layer of uncured silicone rubber or the like and embedding in one side of the silicone rubber layer a material which will impart a fabric texture to the one surface. The silicone rubber is then cured to produce a sheet having one surface which is smooth and one which has a fabric texture. The fabric embedded in the membrane layer can be a gauze or mesh or other equivalent, either coated or uncoated with a polymer, or it can be the fabric-textured sheets prepared by the process of FIG. 1. If the fabric sheet is coated with a polymer, the fabric sheet is optionally leached out to create a network of voids at one side of the sheet corresponding in configuration to the leached fabric sheet.

Referring to FIG. 5, a supporting or forming surface such as plate 50 is immersed in a bath 52 of silicone rubber to coat each surface of the plate with a layer 53 of silicone rubber (see FIG. 5B). Since a main concern is the eventual separation of the finished polymeric sheet intact from plate 50, it is desirable to employ a non-sticking, high-release silicone rubber in bath 52 and a plate 50 having a smooth surface with good release or non-stick properties. Removal of the silicone rubber from the plate becomes a serious problem because normally the silicone rubber layer must be kept very thin, e.g., about 0.2 to 2 mils, in order to obtain desirable water vapor phase transfer rates. The thinness of the sheet detracts from its strength, and unless care is taken, the sheet can tear or otherwise rupture as it is being separated from the support plate. This tendency can be greatly minimized by using a combination of a high-release silicone rubber as the layer in contact with plate 50 and a plate with a non-sticking surface.

Plates 50 having a smooth, highly polished or mirror surface are preferred. For example, metal plates surface-coated with chrome are quite satisfactory, as is highly polished metal foil such as aluminum foil. In addition, any smooth surface of low surface tension can be used, including teflon, polyethylene, polypropylene, teflon coated metal, and the like. Release agents or non-stick agents such as various polyvinylchlorides, soaps and other fatty materials can also be advantageously applied to the surface of plate 50 before it is immersed in bath 52.

The silicone rubber in bath 52 is preferably one which is characterized by high-release or non-stick properties. For example, a preferred silicone rubber for bath 52 is one which, after curing, can be separated intact from plate 50 by the application of a 180 degree peel strength of less than about 50, preferably about 40 or less, especially less than about 25, particularly less than about 15, grams per inch. As used herein, 180 degree peel strength is the maximum force required to peel away intact an ultra-thin (i.e., about 2 mils or less in thickness) strip of material at an angle of 180 degrees, divided by the width of the strip of material. For example, if a strip dimension was 1 inch by 3 inch and the direction of peel was substantially perpendicular to the 1 inch dimension, the strip width to be used in calculating the peel strength would be the one inch dimension, not the three inch dimension.

If peel strengths become excessive, the silicone rubber sheet, because of its thinness and relatively low strength, tends to tear or rupture in the effort to remove it from plate 50. This problem cannot be overcome by resorting to increased sheet thicknesses because, once the sheet thickness exceeds the ultra-thin level of about 2 mils, the water vapor phase transfer rate declines sharply to values which are too low to permit usage of the sheet as a burn dressing.

General Electric's RTV-615 silicone rubber is one example of a high-release silicone rubber preferred for use in bath 52. It is a dimethyl type silicone rubber with a relatively low molecular weight. Another high-release silicone rubber, suitable for bath 52, is Dow Corning's MDX-4-4210 Elastomer.

Of course, other materials besides silicone rubbers can be used in bath 52, provided they are capable of providing water vapor phase transfer rates comparable to silicone rubbers. The problem with many materials is that they have much lower permeabilities to water vapor than silicone rubbers, making it necessary to use such thin films of the materials in order to obtain acceptable water vapor phase transfer rates that the strength of the films is too low for practical usage. The polymer in bath 52 could be any non-sticking, high-release polymer which could be separated from plate 50 with a 180 degree peel strength of less than about 50 grams per inch and which would have water vapor phase permeability characteristics essentially equivalent to those of silicone rubbers.

The coated forming plate 54 then is preferably but not necessarily air-dried at room temperature for about 15 minutes to two hours to evaporate the solvent from the silicone rubber coating and increase the concentration of silicone rubber on the plate.

The dried plate subsequently is immersed in a second bath 58 of a silicone rubber, which can be of a different type than is used in bath 52, in order to add to each side thereof a second layer 60 of silicone rubber (see FIG. 5C). The silicone rubber in bath 58 is selected for its high tensile strength and tear strength characteristics. The high-release silicone rubbers used in bath 52 generally tend to have poor tensile and tear strengths. To compensate for this, bath 58 builds onto the first silicone rubber layer 53 a second layer 60 to add tensile and tear strengths to the finished sheet. In general, any silicone rubber can be used in bath 58 which, upon curing, has a tensile strength for a 25 mil thick cured film of at least about 400, preferably at least about 700, especially at least about 750, pounds per square inch and a tear strength for a 25 mil thick cured film of at least about 20, preferably at least about 25, especially at least about 75, pounds per inch.

Polymers other than silicone rubbers could be used in bath 58 provided they have the above strength characteristics and water vapor phase transfer rates equivalent to those of silicone rubber.

The plate 70 from the second dip tank is then preferably although not necessarily air-dried in the same manner as described above for plate 54.

General Electric's RTV-7000 silicone rubber (now discontinued) and Dow Corning's MDX-4-4210 Elastomer, as well as their equivalents, are examples of silicone rubbers which have been found suitable for use in bath 58. RTV-7000 has a molecular weight after cure which is substantially greater than that of the RTV-615 silicone rubber of bath 52.

The amount of silicone rubber applied to the plate in baths 52 and 58 can be varied as desired by altering such variables as the concentration of solids in the baths, the residence time in the baths and the number of times the plate is dipped into the baths. Illustratively, the concentration of solids in the baths is about 10 to 60%, and anywhere from 1 to 5 dips of a few seconds duration, e.g., 5 to 60 seconds, normally suffices.

Illustratively, only enough of the high-release silicone rubber is applied in bath 52 to form a uniform layer 53 (see FIG. 5B) of sufficient thickness to cover the surface of support plate 50 and thus facilitate easy release of the finished polymeric sheet from the plate. Normally, only enough silicone rubber is applied to plate 50 in bath 52 to form a layer of about 1 mil or less in the finished sheet and preferably about 0.1 to 0.3 mil. This thin layer 53 forms one part of a transparent, pinhole-free, anti-microbial barrier layer 54, while the layer 60 of silicone rubber applied in bath 58 forms the other part.

The high tensile strength, high tear strength silicone rubber used in bath 58 is applied to the plate in sufficient amounts to provide an overall membrane thickness (which includes the thickness of the high-release silicone rubber layer 53) of about 2 mils or less in the finished polymeric sheet and preferably about 0.5 to 1.5 mils. Illustratively, the thickness of the high strength layer 60 can vary from about 0.2 to 2 mils in the finished membrane and preferably is about 0.5 to 1.5 mils.

Because the water vapor phase transfer rate is strongly dependent on the overall thickness of the pinhole-free membrane 54 formed by the two layers 53, 60 of silicone rubber picked up in baths 52 and 58, respectively, it is important that the overall thickness of the membrane portion of the finished sheet be kept highly uniform, e.g., ± about 0.2 mil. The vertical dipcoating techniques shown in FIG. 5 have been especially useful in producing sheets, the membrane component of which is of substantially uniform thickness throughout, at least for sheets whose vertical dimension does not exceed about 12 inches. This results in finished polymeric sheets of highly uniform water vapor phase transfer rate characteristics, an important consideration in a burn dressing.

Although FIG. 5 depicts the application of two silicone rubbers having different characteristics to plate 50 in two separate steps, it is to be understood that, in accordance with the process shown in FIG. 5, acceptable laminates could also be produced by fabricating the pinhole-free membrane layer 54 from a single silicone rubber material by one or more immersions of plate 50 in a single bath instead of two. For example, the pinhole free membrane 54 could be formed solely from RTV-615 silicone rubber, especially in applications where water vapor phase transfer rates were not particularly important, so that strength could be increased by increasing the overall thickness of the RTV-615 rubber. Similarly, the pinhole free membrane could be formed solely from RTV-7000 silicone rubber or equivalents thereof in applications where water vapor phase transfer rates were not particularly important, so that thickness could be increased to avoid tearing or rupturing the sheet when it was removed from plate 50.

Baths 52 and 58 comprise a liquid which contains a polymer. The baths can be a solution or dispersion of the polymer, a latex, or any other form of the polymer which will coat the surface of plate 50 with polymer.

If plate 50 is immersed more than one time in baths 52 or 58, the dipped plates can be optionally dried and/or cured or partially cured between each dip, as well as after the final dip. Any combination of drying alone or drying plus curing could be employed after each dip. Preferably at least one curing step is carried-out before the final dipping of plate 50 in a polymer bath.

Returning now to FIG. 5, the next step following build-up of the membrane layer 54 on plate 50 is to apply, to the outermost layer 60 of the silicone rubber membrane, the material which will provide the fabric texture at one side of the finished sheet. Normally, this is done by applying to layers 60 on the air dried plate 70 a sheet 71 having a coarse fabric texture or other type of coarse or rough surface (see FIG. 5D). Sheets 10, 17, 20 and 33, discussed above in connection with FIG. 1, are examples of the sheet materials which can be used as sheet 71. The nature of sheets 10, 17, 20 and 33 has already been explained in detail. Sheets 10 and 17 are preferred sources of sheet 71 for this embodiment of the invention. Although FIGS. 5D-5E show sheet 71 as being composed of a plurality of strands 71' separated by open spaces 72, sheets 17, 20 and 33 (from FIGS. 1B", 1C" and 1D"), which have no open spaces between the strands, could also be employed as sheet 71.

For the case where sheet 10 from FIG. 1 is used, the sheet preferably will stretch or elongate at least about 100% and preferably about 100 to 300% in each direction. For example, sheet 10 preferably will stretch 100% in a given direction by the application of a force less than about 0.5 pound (for a 1×3 inch strip) and will stretch 200% in a given direction by the application of a force less than about 3 pounds on the same basis. Sheet 10 preferably also has good wicking and liquid absorption characteristics to aid in removing liquids from a wound site at medically acceptable rates. Sheet 71 is preferably formed from a plurality of multifilament yarn strands.

Once sheet 71 has been placed on the silicone rubber layer 60, it is forced into layer 60 deep enough to form a good bond therewith but not deep enough to pierce through to the surface of the support plate 50 or to totally embed sheet 71 in the silicone rubber (see FIG. 5E). It is important that one side of sheet 71 remain exposed and substantially silicone rubber-free, so as to provide the coarse fabric-like surface in the finished sheet for adherence to the wound area and so as to not unduly impair the wettability characteristics of the fabric texture surface of the sheet.

The silicone rubber in layers 53 and 60 is then cured while one side of sheet 71 is embedded in the silicone rubber to bond sheet 71 to the pinhole-free silicone rubber membrane portion 54. This is conveniently done by sandwiching plate 70 with its adhering sheets 71 between two sheets 73 of cured silicone rubber whose surfaces adjacent sheet 71 are preferably covered by a material, such as aluminum foil or a relatively thick layer of nylon fabric. The resulting composite is then placed between two platens 75 of a conventional press, which may be heated by electrical resistance wires 77. Pressure is applied to the composite while it is being heated by the platens to cure the silicone rubber. Enough pressure is used to embed sheet 71 to the desired level in the silicone rubber. The pressure selected can depend on a number of factors, such as the viscosity of the silicone rubber and the percent open area of sheet 71. Illustratively, pressures of about 10 to 200 psi suffice for many applications. Curing temperatures and times for silicone rubbers are well known to those skilled in the art. Illustrative cure cycles involve treatments at room temperature to about 200° C. for about 1.5 to 48 hours, e.g., a treatment at 100° C. for 2 hours.

As the silicone rubber cures, it securely bonds to the individual strands 71' of sheet 71, thereby anchoring sheet 71 to the pinhole-free, cured, silicone rubber, membrane portion 54', composed of cured silicone rubber layers 53' and 60', as best seen in FIG. 5E. The curing step will also cure any polymer on the surfaces of sheet 71. For example, if sheet 71 originates from sheet 17 of FIG. 1, the polymer 12, 12' and 12" on sheet 71 will cure in the curing step.

After curing, the composite 80 of membrane 54' and sheet 71 can take one of two routes, depending upon the nature of sheet 71 and the desired end product. If sheet 71 originated from sheets 10, 17, 20 or 33 of FIG. 1 and if there is no need to remove the skeleton formed by the presence of sheet 10 in sheets 17 and 20, the composite 80 of membrane 54' and sheet 71 is separated from plate 50 to produce the finished polymeric sheet 81 having, on one side, a generally smooth even surface 82 and, on the other side, a coarse, uneven, fabric-like surface 83, as best seen in FIGS. 5F and 5G. FIG. 5F exemplifies the situation where sheet 71 was a sheet of multifilament strands 14, each containing a plurality of individual monofilants 15 (such as sheet 10 in FIGS. 1 and 1A) which had not been coated with a polymer prior to its application to the silicone rubber layer 60. It is evident that, if sheets 17 or 20 from FIG. 1 were used instead of sheet 10, the voids 16 between the individual filaments 15 in each yarn strand 14 (see FIG. 5F) would be filled with cured polymer 21 (as shown in FIGS. 1C to 1C" and 5G), and each multifilament strand 14 would be encased within a sheath of cured polymer 21' (as also shown in FIG. 5G), the thickness of which would depend on the degree of polymer coating on sheets 17 and 20. In short, the finished sheet would be the same as the sheet shown in FIG. 5F, except that the voids 16 in FIG. 5F would be filled with cured polymer 21, 21', as shown in FIG. 5G. If sheet 33 from FIG. 1 was used as sheet 71, the filaments 15 would have already been leached out, so that the finished sheet, after removal from plate 50, would be as shown in FIG. 5I, with the voids 32 replacing the former location of the filaments 15.

On the other hand, if sheet 71 originated from sheets 10, 17 or 20 in FIG. 1 and it is desired to remove the skeleton sheet 10 contained therein to provide a network of elongated continuous voids in the sheet similar to voids 32 and 32' in FIGS. 1D to 1D", the composite sheet 80 (see FIG. 5E) is immersed in a solvent 90 in which the skeleton sheet 10 is soluble but in which the cured polymer coating on the skeleton sheet is substantially insoluble. The solvent 90 leaches or dissolves out the skeleton sheet 10, creating a plurality of elongated channels or voids 32, 32' in the finished polymeric sheet 93 (see FIGS. 5H–5I), as described above in connection with FIGS. 1D to 1D". The nature of the coarse surface 83 of the finished polymeric sheet 93 and the voids 32, 32' in sheet 93 depends on the nature of the skeleton sheet 10. If sheet 10 was composed of a multifilament yarn which had not been coated with a polymer prior to its application to the silicone rubber membrane layer 54, the finished product would appear as in FIG. 5H, with a combination of internal voids 32 and surface voids 32' where filaments 15 had once been (compare FIGS. 5F and 5H). If sheet 10 had been coated with a polymer prior to its application to membrane layer 54, the finished product would appear as in FIG. 5I. It can be appreciated that the coarse surface 83 of polymeric sheet 93 in FIG. 5I is essentially sheet 33 from FIG. 1 and, accordingly, can be varied as desired in the manner discussed above for sheet 33 and as described in FIGS. 1D to 1D".

The skeleton sheet 10 can, of course, be leached from the composite 80 either before or after its separation from plate 50. Preferably the sheet is leached prior to separation from plate 50, provided plate 50 is substantially insoluble in the leaching solvent, and is then air-dried and separated from plate 50 to produce the finished polymeric sheet 93.

As shown in FIGS. 5H and 5I, polymeric sheet 93 has a smooth uniform surface 82 on one side and a coarse, fabric-textured surface 83 on the other. The coarse surface 83 in FIG. 5I comprises a plurality of cured silicone rubber ribs or struts 33', each containing a plurality of filamentary voids 32 therein where the leached skeleton filaments 15 were at one time located. As pointed out in connection with FIGS. 1D, 2 and 2', ribs 33' could also contain elongated surface channels such as channels 32' in FIGS. 1D, 2 and 2', depending upon the extent to which the leached skeleton strands 14 were coated with polymer in the process of preparation.

The finished polymeric sheets 81 and 93 have a smooth-surfaced, thin, pinhole-free, substantially non-porous and voids-free, non-foamed membrane layer 54' on one side thereof which has antimicrobial barrier layer properties and desirable water vapor phase transfer rates. The other side of sheets 81 and 93 has a fabric texture imparted to it by the ribs 14 (FIG. 5F), 24 (FIG. 5G) or 33' (FIG. 5I) joined to membrane 54' or by the elongated voids 32' (FIG. 5H). Sheets 81 and 93 can be formed from one or more polymeric entities. The axis of most of the elongated channels 32, 32' and of the ribs is generally parallel to the plane of sheets 81 and 93, as discussed above in connection with sheet 33. The polymeric sheets 81 and 93 also are very thin and drapable.

The finished polymeric sheets 81 and 93 have properties similar to those discussed above for the sheets 33 produced by the process of FIG. 1. The water vapor phase transfer rate is a function of the thickness of the pinhole-free, anti-microbial barrier or membrane layer 54' and the open area of the fabric-side 83 of the respective sheets. Generally, it is necessary to keep the membrane layer 54' quite thin, e.g., 2 mils or less, in order to obtain water vapor phase transfer rates which approximate those of human skin. The ribs 14, 21' and 33' in sheets 81 and 93 are normally significantly thicker than the membrane 54' and illustratively are about 10 to 60 mils, preferably about 15 to 35 mils, in thickness.

Wettability of the coarse or fabric-textured sides of polymeric sheets 81 and 93 is important in many medical applications. Wettability is defined and compared herein by applying, to the fabric-textured side of a polymeric sheet of the invention, a 0.004 cubic centimeter drop of 1% by weight Congo Red dye in water. The diameter of the spread of the dye solution, as absorbed into the sheet surface, is then measured, and the area of the spread is computed from the measured diameter. The time required for the dye to be completely absorbed into the sheet surface, as viewed with the naked eye, also is measured. Higher wetted area values and lower times for absorption mean increased wettability characteristics. Using this test procedure, illustrative spread areas of anywhere from approximately 0.15 to 1, preferably at least about 0.4, especially at least about 0.6, square centimeter and absorption times of about 0 seconds to 6 minutes, preferably less than about 1 minute, especially less than about 20 seconds, particularly less than about 2 seconds, quite particularly significantly less than about 1 second, i.e., about 0 seconds, have been obtained with the fabric-textured sides of the polymeric sheets of the invention, when such fabric sides have been formed from sheets of multifilament yarns. The variations in wettability can be largely attributed to differences in the materials and structures used to form the fabric-textured sides of the polymeric sheets of the invention. Such variations also indicate

UNITED STATES PATENT AND TRADEMARK OFFICE
CERTIFICATE OF CORRECTION

PATENT NO. : 4,175,557
DATED : November 27, 1979
INVENTOR(S) : John H. Hung

It is certified that error appears in the above-identified patent and that said Letters Patent are hereby corrected as shown below:

in the Abstract, line 20, "fibrolastic" should be -- fibroblastic -- ;

at column 13, line 30, "silicon" should be -- silicone -- ;

at column 13, line 38, "rinshed" should be -- rinsed -- ;

at column 22, line 15, "fabrictextured" should be -- fabric-textured -- ; and at column 26, line 26, "would" should be -- wound -- .

Signed and Sealed this

*First* Day of *July 1980*

[SEAL]

*Attest:*

SIDNEY A. DIAMOND

*Attesting Officer*     *Commissioner of Patents and Trademarks* vapor phase transfer rate of about 2 to 20 mg./hr.-cm.$^2$, two dimensional elongation of at least about 100% in each direction, and an open area between the ribs of zero to about 60%.

2. The wound covering of claim 1 wherein the polymer of the first layer has a 180 degree peel strength of less than about 50 grams per inch and the polymer of the second layer has a tensile strength and tear strength for a 25 mil thick cured film of at least about 700 pounds per square inch and at least about 25 pounds per inch, respectively.

3. The wound covering of claim 1 further including exteriorly located elongated continuous channels in the surface of the layer of fabric texture forming the other surface of the wound covering; the exteriorly located channels extending substantially parallel to the plane of the layer of fabric texture.

4. The wound covering of claim 1 wherein the elongated continuous channels are of a filamentary configuration and have a length to diameter ratio of about 100 and a diameter of about 0.1 to 5 mils.

5. The wound covering of claim 1 wherein the polymer of the first layer has a 180 degree peel strength of about 40 or less grams per inch and the polymer of the second layer has a tensile strength and tear strength for a 25 mil thick cured film of at least about 750 pounds per square inch and at least about 75 pounds per inch, respectively.

6. The wound covering of claim 5 wherein the polymer of the first and second layers is silicone rubber.

7. The wound covering of claim 6 wherein the silicone rubber of the first and second layers is the same silicone rubber.

8. The wound covering of claim 1 wherein the layer of fabric texture has a water vapor phase transfer rate of about 2 to 10 mg./hr.-cm.$^2$ and an open area of about 10 to 50%.

9. The wound covering of claim 8 wherein the layer of fabric is formed from a silicone rubber.

10. A drapable wound covering having a fabric texture on one surface thereof, comprising:
(a) a first layer of cured high-release non-sticking polymer forming one surface of the wound covering;
(b) a second layer of cured polymer having a tensile strength and tear strength for a 25 mil thick cured film thereof of at least about 400 pounds per square inch and at least about 20 pounds per inch, respectively, joined to the first layer of polymer; and
(c) a third layer of fabric texture joined to the second layer of polymer and forming the other surface of the wound covering, the wound having a water vapor phase transfer rate of about 2 to 10 mg./hr.-cm.$^2$, two dimensional elongation of at least about 100% in each direction, and antimicrobial barrier layer properties; and
wherein the layer of fabric texture is an integral, continuous, non-laminated, substantially non-woven, non-fibrous, non-filamentary, non-foamed, drapable polymeric sheet, each side of which has a fabric texture; the sheet comprising a plurality of interbonded continuous polymeric ribs defining between them recessed portions on each side of the sheet; the ribs containing a plurality of elongated continuous channels interiorly located therein which extend in a direction generally parallel to the plane of the sheet to form a network of voids within the ribs which extend continuously throughout the ribs; and the sheet having a water vapor phase transfer rate of about 2 to 20 mg./hr.-cm.$^2$, two dimensional elongation of at least about 100% in each direction, and an open area between the ribs of zero to about 60%.

11. The wound covering of claim 10 further including exteriorly located elongated continuous channels in the surface of the layer of fabric texture forming the other surface of the wound covering; the exteriorly located channels extending substantially parallel to the plane of the layer of fabric texture.

12. The would covering of claim 10 wherein the elongated continuous channels are of a filamentary configuration and have a length to diameter ratio of about 100 and a diameter of about 0.1 to 5 mils.

13. The wound covering of claim 10 wherein the polymer of the first layer has a 180 degree peel strength of less than about 50 grams per inch and the polymer of the second layer has a tensile strength and tear strength for a 25 mil thick cured film of at least about 700 pounds per square inch and at least about 25 pounds per inch, respectively.

14. The wound covering of claim 13 wherein the polymer of the first layer has a 180 degree peel strength of about 40 or less grams per inch and the polymer of the second layer has a tensile strength and tear strength for a 25 mil thick cured film of at least about 750 pounds per square inch and at least about 75 pounds per inch, respectively.

15. The wound covering of claim 14 wherein the polymer of the first and second layers is silicone rubber.

16. The wound covering of claim 15 wherein the silicone rubber of the first and second layers is the same silicone rubber.

17. The wound covering of claim 10 wherein the layer of fabric texture has a water vapor phase transfer rate of about 2 to 10 mg./hr.-cm.$^2$ and an open area of about 10 to 50%.

18. The wound covering of claim 17 wherein the layer of fabric texture is formed from a silicone rubber.

* * * * *

UNITED STATES PATENT AND TRADEMARK OFFICE
CERTIFICATE OF CORRECTION

PATENT NO. : 4,175,557
DATED : November 27, 1979
INVENTOR(S) : John H. Hung

It is certified that error appears in the above-identified patent and that said Letters Patent are hereby corrected as shown below:

in the Abstract, line 20, "fibrolastic" should be -- fibroblastic -- ;

at column 13, line 30, "silicon" should be -- silicone -- ;

at column 13, line 38, "rinshed" should be -- rinsed -- ;

at column 22, line 15, "fabrictextured" should be -- fabric-textured -- ; and at column 26, line 26, "would" should be -- wound -- .

Signed and Sealed this

First Day of July 1980

[SEAL]

Attest:

SIDNEY A. DIAMOND

Attesting Officer

Commissioner of Patents and Trademarks